US010485257B2

(12) United States Patent
Markosyan et al.

(10) Patent No.: US 10,485,257 B2
(45) Date of Patent: Nov. 26, 2019

(54) METHOD OF MAKING STEVIOL GLYCOSIDES

(71) Applicants: PureCircle Sdn Bhd, Kuala Lumpur (MY); The Coca-Cola Company, Atlanta, GA (US)

(72) Inventors: Avetik Markosyan, Yerevan (AM); Cyrille Jarrin, Muret (FR); Patrick Robe, Lanta (FR); Rob ter Halle, Beziege (FR); Indra Prakash, Alpharetta, GA (US); Venkata Sai Prakash Chaturvedula, Alpharetta, GA (US)

(73) Assignee: PureCircle Sdn Bhd, Kuala Lumpur (MY)

( * ) Notice: Subject to any disclaimer, the term of this patent is extended or adjusted under 35 U.S.C. 154(b) by 198 days.

(21) Appl. No.: 15/400,325

(22) Filed: Jan. 6, 2017

(65) Prior Publication Data
US 2017/0112176 A1 Apr. 27, 2017

Related U.S. Application Data

(60) Continuation of application No. 14/954,213, filed on Nov. 30, 2015, now abandoned, which is a division of application No. 14/469,076, filed on Aug. 26, 2014, now Pat. No. 9,243,273, which is a continuation of application No. PCT/US2013/030439, filed on Mar. 12, 2013.

(60) Provisional application No. 61/649,978, filed on May 22, 2012.

(51) Int. Cl.
*C07H 15/256* (2006.01)
*A23L 27/30* (2016.01)
*C12P 19/56* (2006.01)
*C07H 15/24* (2006.01)
*C12P 19/18* (2006.01)

(52) U.S. Cl.
CPC .............. *A23L 27/36* (2016.08); *C07H 15/24* (2013.01); *C12P 19/18* (2013.01); *C12P 19/56* (2013.01); *C12Y 204/01* (2013.01); *A23V 2002/00* (2013.01); *Y02P 20/582* (2015.11)

(58) Field of Classification Search
None
See application file for complete search history.

(56) References Cited

U.S. PATENT DOCUMENTS

| 3,723,410 A | 3/1973 | Persinos |
|---|---|---|
| 4,082,858 A | 4/1978 | Morita et al. |
| 4,171,430 A | 10/1979 | Matsushita et al. |
| 4,219,571 A | 8/1980 | Miyake |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | le Grand et al. |
| 4,892,938 A | 1/1990 | Giovanetto |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,044 B2 | 11/2010 | Abelyan et al. |
| 7,862,845 B2 | 1/2011 | Magomet et al. |
| 8,257,948 B1 | 9/2012 | Markosyan |
| 8,318,459 B2 | 11/2012 | Markosyan |
| 8,647,844 B2 | 2/2014 | Markosyan |
| 8,669,077 B2 | 3/2014 | Prakash |
| 8,735,101 B2 | 5/2014 | Markosyan |
| 9,055,761 B2 | 6/2015 | Markosyan |
| 9,169,285 B2 * | 10/2015 | Prakash .................... A23L 2/60 |
| 9,243,273 B2 * | 1/2016 | Markosyan ............ C07H 15/24 |
| 2002/0132320 A1 | 9/2002 | Wang et al. |

(Continued)

FOREIGN PATENT DOCUMENTS

| BR | P10701736 | 7/2008 |
|---|---|---|
| CA | 2921247 | 2/2015 |

(Continued)

OTHER PUBLICATIONS

A-Glucosyltransferase Treated Stevia, Japan's Specifications and Standards for Food Additives, VIII edition, 2009, p. 257.

(Continued)

*Primary Examiner* — Ralph J Gitomer
(74) *Attorney, Agent, or Firm* — Briggs and Morgan, P.A.; Audrey J. Babcock

(57) ABSTRACT

Methods of preparing highly purified steviol glycosides, particularly rebaudiosides A, D and X are described. The method includes expression of UDP-glucosyltransferases from *Stevia rebaudiana* Bertoni, which are capable converting certain steviol glycosides to rebaudiosides A, D and X. The highly purified rebaudiosides A, D and X, are useful as non-caloric sweetener in edible and chewable compositions such as any beverages, confectioneries, bakery products, cookies, and chewing gums.

7 Claims, 12 Drawing Sheets

Specification includes a Sequence Listing.

(56) References Cited

U.S. PATENT DOCUMENTS

| | | |
|---|---|---|
| 2003/0161876 A1 | 8/2003 | Hansson et al. |
| 2003/0236399 A1 | 12/2003 | Zheng et al. |
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0011215 A1 | 5/2010 | Abelyan et al. |
| 2010/0057024 A1 | 5/2010 | Cavallini et al. |
| 2010/0120710 A1 | 5/2010 | Watanabe et al. |
| 2010/0013756 A1 | 6/2010 | Prakash et al. |
| 2010/0018986 A1 | 7/2010 | Abelyan et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Lui |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214751 A1 | 8/2012 | Markosyan |
| 2012/0214752 A1 | 8/2012 | Markosyan |
| 2013/0171328 A1* | 7/2013 | Kishore ............ C12N 15/8243 426/658 |
| 2014/0227421 A1 | 8/2014 | Markosyan |
| 2014/0296499 A1* | 10/2014 | Chen ................. C07H 15/24 536/18.1 |
| 2014/0357588 A1 | 12/2014 | Markosyan et al. |
| 2015/0031868 A1 | 1/2015 | Lehmann et al. |
| 2015/0157045 A1 | 6/2015 | Markosyan |
| 2016/0031924 A9* | 2/2016 | Prakash ................ A23L 2/60 536/18.1 |
| 2016/0160257 A1* | 6/2016 | Broers ................ A23L 2/60 536/18.1 |
| 2017/0196247 A1* | 7/2017 | Markosyan ........ A23C 9/1307 |
| 2018/0320211 A1* | 11/2018 | Du ..................... C12P 19/56 |

FOREIGN PATENT DOCUMENTS

| | | |
|---|---|---|
| CN | 1049666 | 3/1991 |
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |

(56) References Cited

FOREIGN PATENT DOCUMENTS

| | | |
|---|---|---|
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009108680 | 9/2009 |
| WO | 2010118218 | 10/2010 |
| WO | 2011046423 | 4/2011 |
| WO | 2011059954 | 5/2011 |
| WO | 2011/153378 A1 † | 12/2011 |
| WO | 2011153378 | 12/2011 |
| WO | 2012082493 | 6/2012 |
| WO | 2012082677 | 6/2012 |
| WO | 2013022989 | 2/2013 |
| WO | 2014122227 | 8/2014 |
| WO | 2014122328 | 8/2014 |

OTHER PUBLICATIONS

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside a from stevia glycosides by a novel adsorbent with pyridyl group", Science in China, vol. 42, No. 3 1999, 277-282.
Chen, et al., "Selectivity of polymer adsorbent in adsorptive separations of stevia diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the Stevia plant", Chemistry in Britain, Oct. 1986, 915-916, 918.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
Fuh, , "Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, dated Aug. 5, 2011.
International Search Report and Written Opinion of PCT/US2011/047498, dated Dec. 22, 2011.
International Search Report and Written Opinion of PCT/US2011/047499, dated Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", Stevia: The genus Stevia, Taylor & Francis, 2002, 68-85.
Kinghorn, "Overview", Stevia: The genus Stevia, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al. "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in Fixed-bed column with zeolites", Brazilian Journal of Chemical Engineering, vol. 21, No. 3 2004, 449-458.
Moraes, et al., "Clarification of Stevia rebaudiana (Bert.) Bertoni extract adsorption in modified zeolites", Acta Scientiarum, vol. 23, No. 6 2001, 1375-1380.
Ohta et al., "Characterization of Novel Steviol Glycosides from Leaves of Stevia rebaudiana Morita," J. Appl. Glycosi., vol. 57, 199-209, 2010.
Ohtani et al. "Chapter 7. Methods to improve the taste of the sweet principles of Stevia rebaudiana." The Genus Stevia, edited by A. Douglas Kinghom, CRC Press 2001, Taylor and Francis, London and New York, pp. 138-159.
Phillips, K. C., "Stevia: steps in developing a new sweetener", In T.H. Grenby, Editor, Developments in Sweeteners—3, Elsevier 1987, 1-43.
Pol, et al., "Comparison of two different solvents employed for pressurised fluid extraction of stevioside from Stevia rebaudiana: methanol versus water", Anal Bioanal Chem vol. 388 2007, 1847-1857.
Prakash et al., "Development of rebiana, a natural, non-caloric sweetener," Jul. 1, 2008, Food and Chemical Toxicology, vol. 46, Is. 7, Sup. 1, p. S75-S82.
Richman et al., "Fuctional genomics uncovers three glucosyltransferases involved in the synthesis of the major sweet glucosides of Stevia rebaudiana," The Plant Journal, vol. 41 (2005) 56-67.

(56) References Cited

OTHER PUBLICATIONS

Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.

Shi, et al., "Synthesis of bifunctional polymeric adsorbent and its application in purification of Stevia glycosides", Reactive & Functional Polymers, vol. 50 2002, 107-116.

Shibata et al., "Glucosylation of Steviol and Steviol-Glucosides in Extracts from Stevia rebaudiana Bertoni," Plant Physiol. vol. 95, (1991) 152-156.

Starratt, et al., "Rebaudioside F, a diterpene glycoside from Stevia Rebaudiana", Phytochemistry, vol. 59 2002, 367-370.

Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the Web on May 8, 2012) entire document esp. p. 22, Table 1.

Tanaka, O., "Improvement of taste of natural sweeteners", Pure & Appl. Chem., vol. 69, No. 4 1997, 675-683.

Teo, et al., "Validation of green-solvent extraction combined with chromatographic chemical fingerprint to evaluate quality of Stevia rebaudiana Bertoni", J. Sep. Sci, vol. 32 2009, 613-622.

United Nations' Food and Agriculture Organization/Joint Expert Committee on Food Additives (2010) Steviol Glycosides, Compendium of Food Additive Specifications, FAO JECFA Monographs 10, 17-21.

Van der Maarel et al., "Properties and applications of starch-converting enzymes of the a-amylase family," Journal of Biotechnology, vol. 94 (2002) 137-155.

Vasquez, Stimulation of the Gerbil's Gustatory Receptors by Some Potently Sweet Terpenoids, J. Agric. Food Chem., vol. 41, 1305-1310, 1993.

Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.

Yoda, et al., "Supercritical fluid extraction from Stevia rebaudiana Bertoni using CO2 and CO2+ water: extraction kinetics and identification of extracted components", Journal of Food Engineering, vol. 57 2003, 125-134.

Zell, et al. "Investigation of Polymorphism in Aspartame and Neotame Using Solid-State NMR Spectroscopy", Tetrahedron, vol. 56, 2000, 6603-6616.

Zhang, et al., "Membrane-based separation scheme for processing sweetener from Stevia leaves", Food Research International, vol. 33 2000, 617-620.

Prakash, Development of Next Generation Stevia Sweetener: Rebaudioside M,: Foods, 3, 162-175, 2014.

\* cited by examiner
† cited by third party

Co-HPLC Chromatogram of Standard Rebaudioside X and Rebaudioside X Purified from Biotransformation of Rebaudioside D

SEQUENCE LISTING

<160> NUMBER OF SEQ ID NOS: 2

<210> SEQ ID NO 1
<211> LENGTH: 1397

<212> TYPE: DNA
<213> ORGANISM: Escherichia coli

<400> SEQUENCE: 1

| | | | | | |
|---|---|---|---|---|---|
| ccatggccca | tatggaaaac | aaaaccgaaa | ccaccgttcg | tcgtcgtcgc | cgtattattc | 60 |
| tgtttccggt | tccgtttcag | ggtcatatta | atccgattct | gcagctggca | aatgtgctgt | 120 |
| atagcaaagg | ttttagcatt | accatttttc | ataccaattt | taacaaaccg | aaaaccagca | 180 |
| attatccgca | ttttaccttt | cgctttattc | tggataatga | tccgcaggat | gaacgcatta | 240 |
| gcaatctgcc | gacacatggt | ccgctggcag | gtatgcgtat | tccgattatt | aacgaacatg | 300 |
| gtgcagatga | actgcgtcgt | gaactggaac | tgctgatgct | ggcaagcgaa | gaagatgaag | 360 |
| aagttagctg | tctgattacc | gatgcactgt | ggtattttgc | acagagcgtt | gcagatagcc | 420 |
| tgaatctgcg | tcgtctggtt | ctgatgacca | gcagcctgtt | taactttcat | gcacatgtta | 480 |
| gcctgccgca | gtttgatgaa | ctgggttatc | tggatccgga | tgataaaacc | cgtctggaag | 540 |
| aacaggcaag | cggttttccg | atgctgaaag | tgaaagatat | caaaagcgcc | tatagcaatt | 600 |
| ggcagattct | gaaagaaatt | ctgggcaaaa | tgattaaaca | gaccaaagca | agcagcggtg | 660 |
| ttatttggaa | tagctttaaa | gaactggaag | aaagcgaact | ggaaaccgtg | attcgtgaaa | 720 |
| ttccggcacc | gagctttctg | attccgctgc | cgaaacatct | gaccgcaagc | agcagcagcc | 780 |
| tgctggatca | tgatcgtacc | gttttcagt | ggctggatca | gcagcctccg | agcagcgttc | 840 |
| tgtatgttag | ctttggtagc | accagcgaag | ttgatgaaaa | agatttctg | gaaattgccc | 900 |
| gtggtctggt | tgatagcaaa | cagagctttc | tgtgggttgt | tcgtccgggt | tttgttaaag | 960 |
| gtagcacctg | ggttgaaccg | ctgccggatg | ttttctggg | tgaacgtggt | cgtattgtta | 1020 |
| aatgggttcc | gcagcaagaa | gttctggcac | acggcgcaat | tggtgcattt | tggacccata | 1080 |
| gcggttggaa | tagcaccctg | gaaagcgttt | gtgaaggtgt | tccgatgatt | tttagcgatt | 1140 |
| ttggtctgga | tcagccgctg | aatgcacgtt | atatgagtga | tgttctgaaa | gtgggtgtgt | 1200 |
| atctggaaaa | tggttgggaa | cgtggtgaaa | ttgcaaatgc | aattcgtcgt | gttatggtgg | 1260 |
| atgaagaagg | tgaatatatt | cgtcagaatg | cccgtgttct | gaaacagaaa | gcagatgtta | 1320 |
| gcctgatgaa | aggtggtagc | agctatgaaa | gcctggaaag | tctggttagc | tatattagca | 1380 |
| gcctgtaata | actcgag | | | | | 1397 |

<210> SEQ ID NO 2
<211> LENGTH: 1442
<212> TYPE: DNA
<213> ORGANISM: Escherichia coli

<400> SEQUENCE: 2

| | | | | | |
|---|---|---|---|---|---|
| ccatggcaca | tatggcaacc | agcgatagca | ttgttgatga | tcgtaaacag | ctgcatgttg | 60 |
| caacctttcc | gtggctggca | tttggtcata | ttctgccgta | tctgcagctg | agcaaactga | 120 |
| ttgcagaaaa | aggtcataaa | gtgagctttc | tgagcaccac | ccgtaatatt | cagcgtctga | 180 |
| gcagccatat | tagtccgctg | attaatgttg | ttcagctgac | cctgcctcgt | gttcaagaac | 240 |
| tgccggaaga | tgccgaagca | accaccgatt | tcatccgga | agatattccg | tatctgaaaa | 300 |
| aagcaagtga | tggtctgcag | ccggaagtta | cccgttttct | ggaacagcat | agtccggatt | 360 |
| ggatcatcta | tgattatacc | cattattggc | tgccgagcat | tgcagcaagc | ctgggtatta | 420 |
| gccgtgcaca | ttttagcgtt | accaccccgt | gggcaattgc | atatatgggt | ccgagcgcag | 480 |
| atgcaatgat | taatggtagt | gatggtcgta | ccaccgttga | agatctgacc | accccctccga | 540 |

```
aatggtttcc gtttccgacc aaagtttgtt ggcgtaaaca tgatctggca cgtctggttc    600
cgtataaagc accgggtatt agtgatggtt atcgtatggg tctggttctg aaaggtagcg    660
attgtctgct gagcaaatgc tatcatgaat ttggcaccca gtggctgccg ctgctggaaa    720
ccctgcatca ggttccggtt gttccggtgg gtctgctgcc tccggaagtt ccgggtgatg    780
aaaaagatga aacctgggtt agcatcaaaa aatggctgga tggtaaacag aaaggtagcg    840
tggtttatgt tgcactgggt agcgaagttc tggttagcca gaccgaagtt gttgaactgg    900
cactgggtct ggaactgagc ggtctgccgt ttgtttgggc atatcgtaaa ccgaaaggtc    960
cggcaaaaag cgatagcgtt gaactgccgg atggttttgt tgaacgtacc cgtgatcgtg   1020
gtctggtttg gaccagctgg gcacctcagc tgcgtattct gagccatgaa agcgtttgtg   1080
gttttctgac ccattgtggt agcggtagca ttgtggaagg tctgatgttt ggtcatccgc   1140
tgattatgct gccgattttt ggtgatcagc cgctgaatgc acgtctgctg gaagataaac   1200
aggttggtat tgaaattccg cgtaatgaag aagatggttg cctgaccaaa gaaagcgttg   1260
cacgtagcct gcgtagcgtt gttgttgaaa aagaaggcga aatctataaa gccaatgcac   1320
gtgaactgag caaaatctat aatgatacca aagtggaaaa agaatatgtg agccagttcg   1380
tggattatct ggaaaaaaac acccgtgcag ttgccattga tcacgaaagc taatgactcg   1440
ag                                                                   1442
```

METHOD OF MAKING STEVIOL GLYCOSIDES

TECHNICAL FIELD

The present invention relates to a biocatalytic process for preparing compositions comprising steviol glycosides, including highly purified steviol glycoside compositions.

INCORPORATION BY REFERENCE OF SEQUENCE LISTING

The text file entitled "PureCircle_22PCT_ST25.txt," created on Mar. 12, 2013, having 5 KB (kilobytes) of data, and filed concurrently herewith, is hereby incorporated by reference in its entirety in this application.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of Stevia rebaudiana Bertoni, a perennial shrub of the Asteraceae (Compositae) family native to certain regions of South America. They are characterized structurally by a single base, steviol, differing by the presence of carbohydrate residues at positions C13 and C19. They accumulate in Stevia leaves, composing approximately 10%-20% of the total dry weight. On a dry weight basis, the four major glycosides found in the leaves of Stevia typically include stevioside (9.1%), rebaudioside A (3.8%), rebaudioside C (0.6-1.0%) and dulcoside A (0.3%). Other known steviol glycosides include rebaudioside B, C, D, E, F and X steviolbioside and rubusoside.

Although methods are known for preparing steviol glycosides from Stevia rebaudiana, many of these methods are unsuitable for use commercially.

Accordingly, there remains a need for simple, efficient, and economical methods for preparing compositions comprising steviol glycosides, including highly purified steviol glycoside compositions.

SUMMARY OF THE INVENTION

The present invention provides a biocatalytic process for preparing a composition comprising a target steviol glycoside by contacting a starting composition comprising a steviol glycoside substrate with UDP-glucosyltransferase, thereby producing a composition comprising a target steviol glycoside comprising one or more additional glucose units than the steviol glycoside substrate.

The starting composition can be any composition comprising at least one steviol glycoside substrate. In one embodiment, the steviol glycoside substrate is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O, a synthetic steviol glycoside or combinations thereof. The starting composition may be commercially available or prepared. The starting composition may comprise a purified steviol glycoside substrate or a partially purified steviol glycoside substrate.

In one embodiment, the steviol glycoside substrate is rubusoside.

In another embodiment, the steviol glycoside substrate is stevioside.

In still another embodiment, the steviol glycoside substrate is rebaudioside A.

In yet another embodiment, the steviol glycoside substrate is rebaudioside D.

The target steviol glycoside can be any known steviol glycoside. In one embodiment, the target steviol glycoside is steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O or a synthetic steviol glycoside.

In one embodiment, the target steviol glycoside is stevioside.

In another embodiment, the target steviol glycoside is rebaudioside A.

In still another embodiment, the target steviol glycoside is rebaudioside D.

In yet another embodiment, the target steviol glycoside is rebaudioside X.

The UDP-glucosyltransferase can be any UDP-glucosyltransferase capable of adding at least one glucose unit to the steviol glycoside substrate to provide the target steviol glycoside. In one embodiment, UDP-glucosyltransferase is produced in a host. The host may be, for example, E. coli, Saccharomyces sp., Aspergillus sp., Pichia sp. In another embodiment, the UDP-glucosyltransferase is synthesized.

The UDP-glucosyltransferase can be provided in any suitable form, including free, immobilized or as a whole cell system. The degree of purity of the UDP-glucosyltransferase may vary, e.g., it may be provided as a crude, semi-purified or purified enzyme preparation(s).

In one embodiment, the UDP-glucosyltransferase is free. In another embodiment, the UDP-glucosyltransferase is immobilized, for example on an inorganic or organic support. In yet another embodiment, the UDP-glucosyltransferase is provided in the form of a whole cell system, for example as a living microbial cell, or in the form of a cell lysate.

In one embodiment, the UDP-glucosyltransferase is any UDP-glucosyltransferase capable of adding at least one glucose unit to rubusoside to form stevioside. In a particular embodiment, the UDP-glucosyltransferase is UGT91D2.

In one embodiment, the UDP-glucosyltransferase is any UDP-glucosyltransferase capable of adding at least one glucose unit to stevioside to form rebaudioside A. In a particular embodiment, the UDP-glucosyltransferase is UGT76G1.

In another embodiment, the UDP-glucosyltransferase is any UDP-glucosyltransferase capable of adding at least one glucose unit to rebaudioside A to form rebaudioside D. In a particular embodiment, the UDP-glucosyltransferase is UGT91D2.

In yet another embodiment, the UDP-glucosyltransferase is any UDP-glucosyltransferase capable of adding at least one glucose unit to rebaudioside D to form rebaudioside X. In a particular embodiment, the UDP-glucosyltransferase is UGT76G1.

Optionally, the method of the present invention further comprises recycling UDP to provide UDP-glucose. In one embodiment, the method comprises recycling UDP by providing a recycling catalyst and a recycling substrate, such that the biotransformation of the steviol glycoside substrate to the target steviol glycoside is carried out using catalytic amounts of UDP-glucosyltransferase and UDP-glucose (FIG. 3).

In one embodiment, the recycling catalyst is sucrose synthase.

In one embodiment, the recycling substrate is sucrose.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In one embodiment, separation produces a composition comprising greater than about 80% by weight of the target steviol glycoside on an anhydrous basis, i.e., a highly purified steviol glycoside composition. In another embodiment, separation produces a composition comprising greater than about 90% by weight of the target steviol glycoside. In particular embodiments, the composition comprises greater than about 95% by weight of the target steviol glycoside.

The target steviol glycoside can be in any polymorphic or amorphous form, including hydrates, solvates, anhydrous or combinations thereof.

Purified target steviol glycosides can be used in consumable products as a sweetener. Suitable consumer products include, but are not limited to, food, beverages, pharmaceutical compositions, tobacco products, nutraceutical compositions, oral hygiene compositions, and cosmetic compositions.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION

Figure 1:
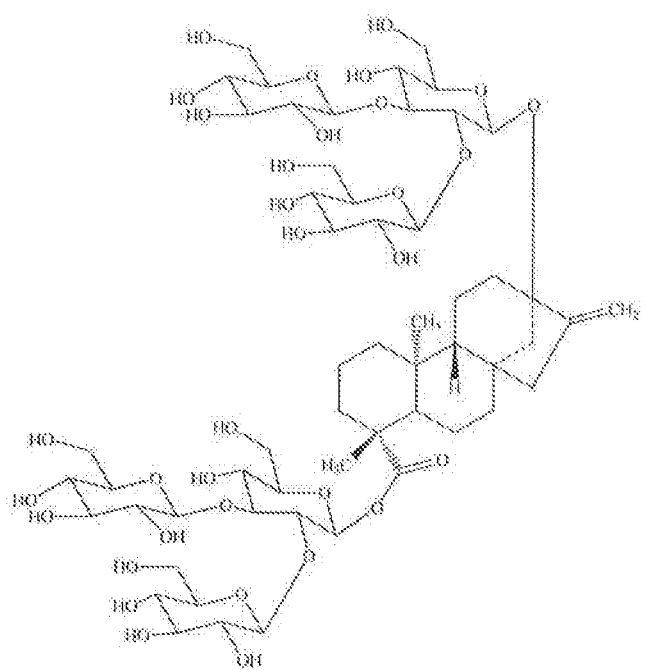
FIG. 1 shows the structure of reb X.
Figure 2:
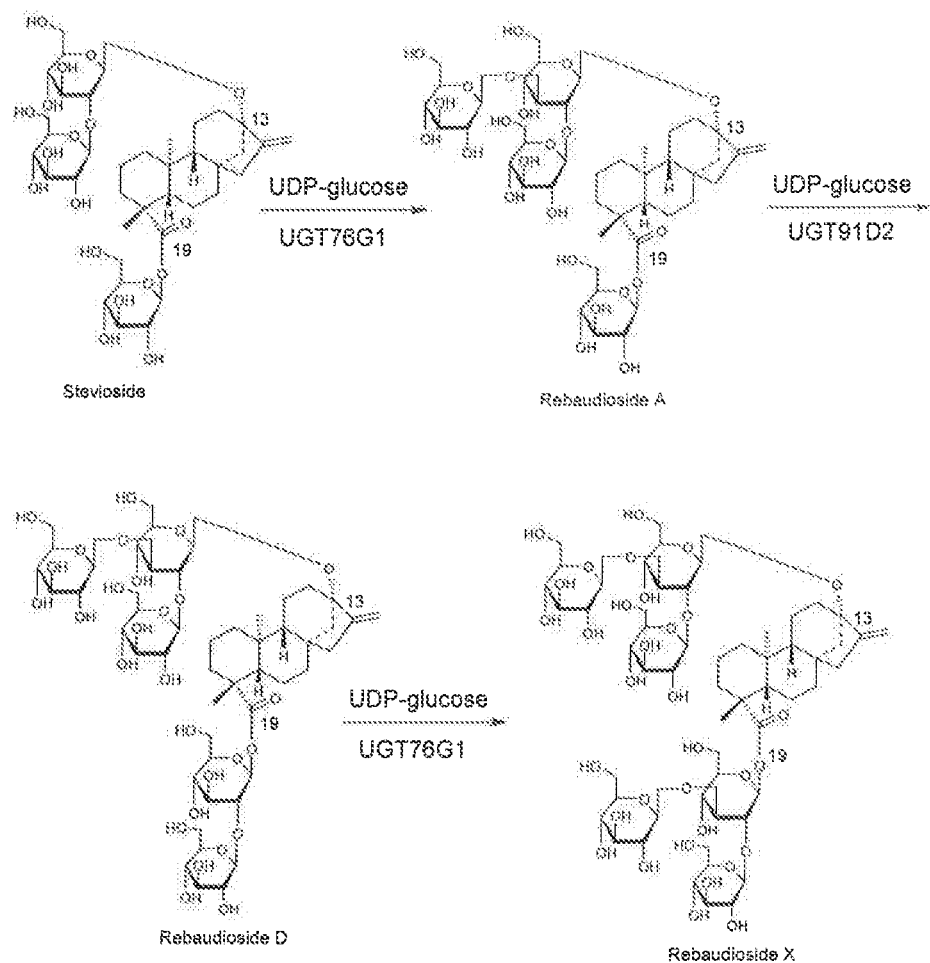
FIG. 2 shows the biocatalytic production of reb X from stevioside.

The present invention provides a biocatalytic process for the preparation of a composition comprising a target steviol glycoside from a starting composition comprising a steviol glycoside substrate, wherein the target steviol glycoside comprises one or more additional glucose units than the steviol glycoside substrate.

One object of the invention is to provide an efficient biocatalytic method for preparing steviol glycosides, particularly stevioside, reb A, reb D and reb X, from other steviol glycosides and/or mixtures thereof.

As used herein, "biocatalysis" or "biocatalytic" refers to the use of natural catalysts, such as protein enzymes, to perform chemical transformations on organic compounds. Biocatalysis is alternatively known as biotransformation or biosynthesis. Both isolated and whole-cell biocatalysis methods are known in the art. Biocatalyst protein enzymes can be naturally occurring or recombinant proteins.

As used herein, the term "steviol glycoside(s)" refers to a glycoside of steviol, including, but not limited to, naturally occurring steviol glycosides, e.g. steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O, synthetic steviol glycosides, e.g. enzymatically glucosylated steviol glycosides and combinations thereof.

Chemical Structures of Steviol and its Glycosides

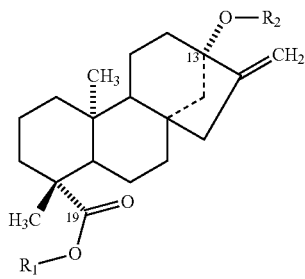

| Compound | $R_1$ | $R_2$ |
|---|---|---|
| Steviol | H | H |
| Steviolmonoside | H | β-Glc |
| Steviol monoglucosyl ester | β-Glc | H |
| Rubusoside | β-Glc | β-Glc |
| Steviolbioside | H | β-Glc-β-Glc (2→1) |
| Stevioside | β-Glc | β-Glc-β-Glc (2→1) |
| Rebaudioside A | β-Glc | β-Glc-β-Glc (2→1) <br> \| <br> β-Glc (3→1) |

-continued

| Compound | R₁ | R₂ |
|---|---|---|
| Rebaudioside D | β-Glc-β-Glc (2→1) | β-Glc-β-Glc (2→1)<br>\|<br>β-Glc (3→1) |
| Rebaudioside X | β-Glc-β-Glc (2→1)<br>\|<br>β-Glc (3→1) | β-Glc-β-Glc (2→1)<br>\|<br>β-Glc (3→1) |

(Glc = glucose)

Starting Composition

As used herein, "starting composition" refers to any composition (generally an aqueous solution) containing one or more steviol glycosides, where the one or more steviol glycosides serve as the substrate for the biotransformation.

In one embodiment, the starting composition comprises one or more steviol glycosides selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N, rebaudioside O or a synthetic steviol glycoside. In a particular embodiment, the starting composition comprises two or more steviol glycosides.

In one embodiment, the starting composition comprises the steviol glycoside substrate rubusoside.

In one embodiment, the starting composition comprises the steviol glycoside substrate stevioside.

In another embodiment, the starting composition comprises the steviol glycoside substrate rebaudioside A.

In yet another embodiment, the starting composition comprises the steviol glycoside substrate rebaudioside D.

The starting composition may be synthetic or purified (partially or entirely), commercially available or prepared. One example of a starting composition useful in the method of the present invention is an extract obtained from purification of *Stevia rebaudiana* plant material (e.g. leaves). Another example of a starting composition is a commercially available *stevia* extract brought into solution with a solvent. Yet another example of a starting composition is a commercially available mixture of steviol glycosides brought into solution with a solvent. Other suitable starting compositions include by-products of processes to isolate and purify steviol glycosides.

In one embodiment, the starting composition comprises a purified steviol glycoside substrate. For example, the starting composition may comprise greater than about 99% of a particular substrate steviol glycoside by weight on a dry basis.

In another embodiment, the starting composition comprises a partially purified substrate steviol glycoside composition. For example, the starting composition contains greater than about 50%, about 60%, about 70%, about 80% or about 90% of a particular substrate steviol glycoside by weight on a dry basis.

In one embodiment, the starting composition comprises purified rubusoside. In a particular embodiment, the starting composition contains >99% rubusoside by weight on a dry basis. In another embodiment, the starting composition comprises partially purified rubusoside. In a particular embodiment, the starting composition contains greater than about 50%, about 60%, about 70%, about 80% or about 90% rubusoside by weight on a dry basis.

In one embodiment, the starting composition comprises purified stevioside. In a particular embodiment, the starting composition contains >99% stevioside by weight on a dry basis. In another embodiment, the starting composition comprises partially purified stevioside. In a particular embodiment, the starting composition contains greater than about 50%, about 60%, about 70%, about 80% or about 90% stevioside by weight on a dry basis.

In another embodiment, the starting composition comprises purified rebaudioside A. In a particular embodiment, the starting composition contains greater than about 99% rebaudioside A by weight on a dry basis. In another embodiment, the starting composition comprises partially purified rebaudioside A. In a particular embodiment, the starting composition contains greater than about 50%, about 60%, about 70%, about 80% or about 90% rebaudioside A by weight on a dry basis.

In yet another embodiment, the starting composition comprises purified rebaudioside D. In a particular embodiment, the starting composition contains greater than about 99% rebaudioside D by weight on a dry basis. In another embodiment, the starting composition comprises partially purified rebaudioside D. In a particular embodiment, the starting composition contains greater than about 50%, about 60%, about 70%, about 80% or about 90% rebaudioside D by weight on a dry basis.

The steviol glycoside component(s) of the starting composition serve as a substrate(s) for the production of the target steviol glycoside(s), as described herein. The target steviol glycoside target(s) differs chemically from its corresponding steviol glycoside substrate(s) by the addition of one or more glucose units.

Target Steviol Glycoside

The target steviol glycoside of the present method can be any steviol glycoside that can be prepared by the process disclosed herein. In one embodiment, the target steviol glycoside is selected from the group consisting of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside X, rebaudioside D, rebaudioside N or rebaudioside O.

In one embodiment, the target steviol glycoside is stevioside. In another embodiment, the target steviol glycoside is reb A. In yet another embodiment, the target steviol glycoside is reb D. In still another embodiment, the target steviol glycoside is reb X.

The target steviol glycoside can be in any polymorphic or amorphous form, including hydrates, solvates, anhydrous or combinations thereof.

In one embodiment, the present invention is a biocatalytic process for the production of stevioside from rubusoside, where the starting composition comprises the steviol glycoside substrate rubusoside. In a particular embodiment, the present invention is a biocatalytic process for the production of stevioside from rubusoside, where the starting composition comprises partially purified rubusoside. In another particular embodiment, the present invention is a biocatalytic process for the production of stevioside from rubusoside, where the starting composition comprises purified rubusoside.

In one embodiment, the present invention is a biocatalytic process for the production of reb A from stevioside, where the starting composition comprises the steviol glycoside substrate stevioside. In a particular embodiment, the present invention is a biocatalytic process for the production of reb A from stevioside, where the starting composition comprises partially purified stevioside. In another particular embodiment, the present invention is a biocatalytic process for the production of reb A from stevioside, where the starting composition comprises purified stevioside.

In another embodiment, the present invention is a biocatalytic process for the production of reb D from reb A, where the starting composition comprises the steviol glycoside substrate reb A. In a particular embodiment, the present invention is a biocatalytic process for the production of reb D from reb A, where the starting composition comprises partially purified reb A. In another particular embodiment, the present invention is a biocatalytic process for the production of reb D from reb A, where the starting composition comprises purified reb A.

In still another embodiment, the present invention is a biocatalytic process for the production of reb X from reb D, where the starting composition comprises the steviol glycoside substrate reb D. In a particular embodiment, the present invention is a biocatalytic process for the production of reb X from reb D, where the starting composition comprises partially purified reb D. In another particular embodiment, the present invention is a biocatalytic process for the production of reb X from reb D, where the starting composition comprises purified reb D.

In a particular embodiment, the target steviol glycoside is present in a mixture. For example, in one embodiment, the target steviol glycoside is reb X present in a mixture. In one embodiment, the purity of the target steviol glycoside is increased relative to the purity of the target steviol glycoside present in the starting composition. For example, the purity of reb X present in the starting composition is increased as a result of carrying out the method of the present invention.

Optionally, the method of the present invention further comprises separating the target steviol glycoside from the starting composition. The target steviol glycoside can be separated by any suitable method, such as, for example, crystallization, separation by membranes, centrifugation, extraction, chromatographic separation or a combination of such methods.

In particular embodiments, the process described herein results in a highly purified target steviol glycoside composition. The term "highly purified", as used herein, refers to a composition having greater than about 80% by weight of the target steviol glycoside on an anhydrous basis. In one embodiment, the highly purified target steviol glycoside composition contains greater than about 90% by weight of the target steviol glycoside on an anhydrous basis, such as, for example, 91% greater than about 92%, greater than about 93%, greater than about 94%, greater than about 95%, greater than about 95%, greater than about 97%, greater than about 98% or greater than about 99% target steviol glycoside content on a dry basis.

In a more particular embodiment, when the target steviol glycoside is reb X, the process described herein provides a composition having greater than about 90% reb X content by weight on a dry basis. In another particular embodiment, when the target steviol glycoside is reb X, the process described herein provides a composition comprising greater than about 95% reb X content by weight on a dry basis.

In another particular embodiment, when the target steviol glycoside is reb D, the process described herein provides a composition greater than about 90% reb D content by weight on a dry basis. In another particular embodiment, when the target steviol glycoside is reb D, the process described herein provides a composition comprising greater than about 95% reb D content by weight on a dry basis.

In still another particular embodiment, when the target steviol glycoside is reb A, the process described herein provides a composition comprising greater than about 90% reb A content by weight on a dry basis. In another particular embodiment, when the target steviol glycoside is reb A, the process described herein provides a composition comprising greater than about 95% reb A content by weight on a dry basis.

In yet another particular embodiment, when the target steviol glycoside is stevioside, the process described herein provides a composition comprising greater than about 90% stevioside content by weight on a dry basis. In another particular embodiment, when the target steviol glycoside is stevioside, the process described herein provides a composition comprising greater than about 95% stevioside content by weight on a dry basis.

In one embodiment, the biocatalytic method of the present invention is carried out more than one time, such that the target steviol glycoside produced by a first biocatalytic process serves as the steviol glycoside substrate (which could also be considered an intermediate target steviol glycoside) for a second biocatalytic process in which the target steviol glycoside is produced.

In a particular embodiment, the present invention provides a biocatalytic process for preparing a composition comprising a target steviol glycoside by contacting a starting composition comprising a steviol glycoside substrate with a UDP-glucosyltransferase, thereby producing a composition comprising an intermediate target steviol glycoside comprising one or more additional glucose units than the steviol glycoside substrate; contacting the composition comprising the intermediate target steviol glycoside with UDP-glucosyltransferase, thereby producing a target steviol glycoside comprising one or more additional glucose units than the intermediate target steviol glycoside. Depending on the number of times the method is carried out, there may be one or more intermediate target steviol glycosides (e.g., a first intermediate target steviol glycoside, a second intermediate target steviol glycoside, a third intermediate target steviol glycoside) involved in the production of the target steviol glycoside.

UDP-glucotransferase

The present method is biocatalytic, i.e., utilizes a biological catalyst. In one embodiment, the biocatalyst is protein enzyme. In a particular embodiment, the biocatalyst is a UDP-glucosyltransferase. The UDP-glucosyltransferase can be any UDP-glucosyltransferase capable of adding at least one glucose unit to the steviol glycoside substrate to provide the target steviol glycoside.

In one embodiment, the UDP-glucosyltransferase is produced in a host, such as a microorganism. For example, a DNA sequence encoding UDP-glucosyltransferase is cloned into an expression vector and transferred into a production host such as a microbe, e.g., a bacteria. Non-limiting examples of suitable hosts include *E. coli*, *Saccharomyces* sp., *Aspergillus* sp., *Pichia* sp. The overexpressed protein can be isolated from the cell extract based on its physical and chemical properties, using techniques known in the art. Representative non-limiting techniques for isolating UDP-glucosyltransferase from a host include centrifugation, electrophoresis, liquid chromatography, ion exchange chromatography, gel filtration chromatography or affinity chromatography.

UDP-glucosyltransferase can be provided as a crude, semi-purified and purified enzyme preparation(s).

In one embodiment, the UDP-glucosyltransferase is free. In another embodiment, the UDP-glucosyltransferase is immobilized. For example, UDP-glucosyltransferase may be immobilized to a solid support made from inorganic or organic materials. Non-limiting examples of solid supports suitable to immobilize UDP-glucosyltransferase include derivatized cellulose or glass, ceramics, metal oxides or membranes. UDP-glucosyltransferase may be immobilized to the solid support, for example, by covalent attachment, adsorption, cross-linking, entrapment or encapsulation.

The reaction medium for conversion is generally aqueous, e.g., purified water, buffer or a combination thereof. In a particular embodiment, the reaction medium is a buffer. Suitable buffers include, but are not limited to, PIPES buffer, acetate buffer and phosphate buffer. In a particular embodiment, the reaction medium is a phosphate buffer. The reaction medium can also be, alternatively, an organic solvent.

In one embodiment, the UDP-glucosyltransferase is provided in the form of a whole cell system, such as a living microbial cell. The whole cell system may optionally be immobilized, as well, utilizing the techniques identified above with respect to immobilization of the enzyme.

In one embodiment, the UDP-glucosyltransferase is any UDP-glucosyltransferase capable of adding at least one glucose unit to rubusoside, thereby producing stevioside. The UDP-glucosyltransferase may be, for example, UGT91D2.

In another embodiment, the UDP-glucosyltransferase is any UDP-glucosyltransferase capable of adding at least one glucose unit to stevioside, thereby producing rebaudioside A. The UDP-glucosyltransferase may be, for example, UGT76G1.

In still another embodiment, the UDP-glucosyltransferase is any UDP-glucosyltransferase capable of adding at least one glucose unit to rebaudioside A, thereby producing rebaudioside D. The UDP-glucosyltransferase may be, for example, UGT91D2.

In yet another embodiment, the UDP-glucosyltransferase is any UDP-glucosyltransferase capable of adding at least one glucose unit to rebaudioside D to form rebaudioside X. The UDP-glucosyltransferase may be, for example, UGT76G1.

Figure 3:
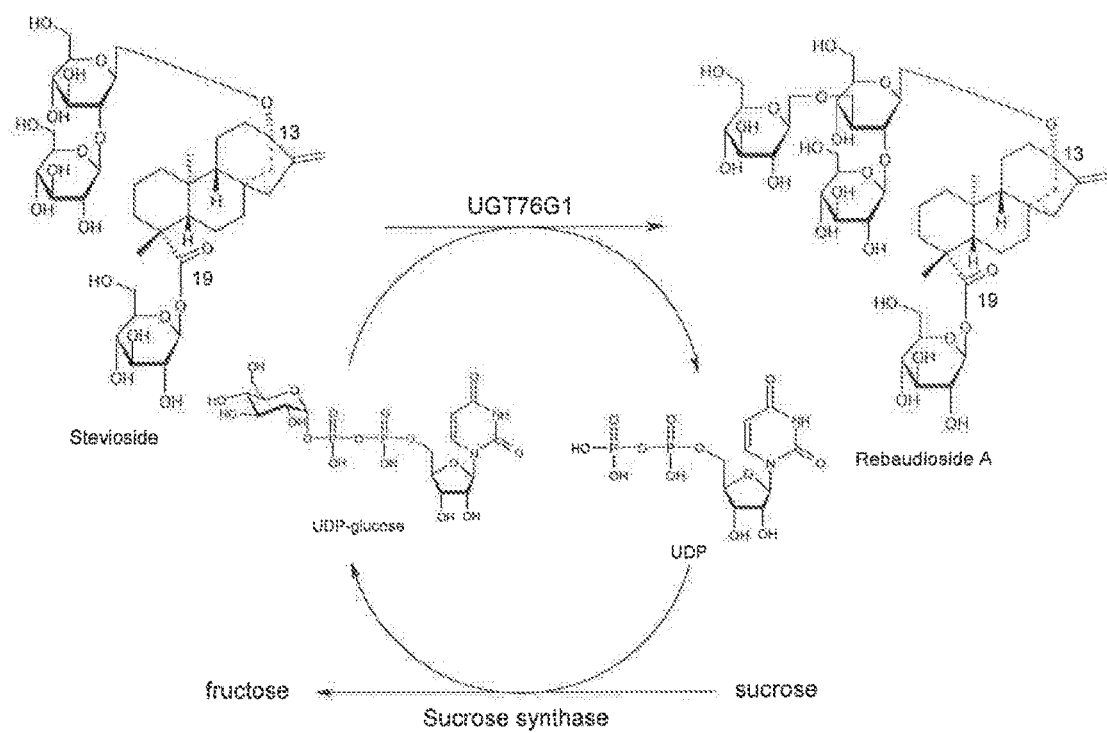
FIG. 3 shows the biocatalytic production of reb A from stevioside using the enzyme UGT76G1 and concomitant recycling of UDP to UDP glucose via sucrose synthase.

Optionally, the method of the present invention further comprises recycling UDP to provide UDP-glucose. In one embodiment, the method comprises recycling UDP by providing a recycling catalyst, i.e., a biocatalyst capable of UDP-glucose overproduction, and a recycling substrate, such that the conversion of the substrate steviol glycoside to the target steviol glycoside is carried out using catalytic amounts of UDP-glucosyltransferase and UDP-glucose (FIG. 3).

In one embodiment, the UDP-glucose recycling catalyst is sucrose synthase.

In one embodiment, the recycling substrate is sucrose.

The Conversion of Rubusoside to Stevioside

In one embodiment, a starting composition comprising rubusoside is contacted with a UDP-glucosyltransferase capable of catalyzing the reaction of UDP-glucose and stevioside to produce stevioside. In one embodiment, the starting composition comprises partially purified rubusoside. In another embodiment, the starting composition comprises purified rubusoside. In a particular embodiment, the starting composition comprises >99% rubusoside. In a particular embodiment, the starting composition comprises greater than about 50%, about 60%, about 70% about 80% or about 90% rubusoside.

In a particular embodiment, the UDP-glucosyltransferase is UGT91D2, which has been described by Joseph et al. (Genbank accession no. ACE87855). It has to be noted that similar sequence was described later in a patent application PCT/US2011/038967 and named UGT91D2e. UGT91D2e shares >95% identity with UGT91D11 (Genbank accession no. AAR06918) and >99% identity with UGT of Joseph et al. (Genbank accession no. ACE87855).

In some embodiments, the UDP-glucosyltransferase, such as UGT91D2, is prepared by expression in a host microorganism. Suitable host microorganisms include, but are not limited to, *E. coli, Saccharomyces* sp., *Aspergillus* sp., *Pichia* sp. In a particular embodiment, UGT91D2 is expressed in *E. coli*.

The UDP-glucosyltransferase, such as UGT91D2, can be provided free or in an immobilized form. The enzyme preparation may be crude, semi-purified and purified. In one embodiment, the UDP-glucosyltransferase is provided as a whole-cell system, e.g., a living microbial cell, or whole microbial cells, cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of rubusoside to stevioside further comprises the addition of compounds other than UDP-glucose, rubusoside and the UDP-glucosyltransferase. For example, in some embodiments, the reaction medium includes $MgCl_2$ and/or $MnCl_2$ The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme sucrose synthase (FIG. 3). Rubusoside is transformed into stevioside with UDP-glucose which is recycled by the reaction between sucrose and UDP. As a consequence, rubusoside and sucrose are used in stoichiometric amounts whereas UDP is present in catalytic amounts.

The reaction can be monitored by suitable method including, but not limited to, HPLC, LCMS, TLC, IR or NMR.

In one embodiment, the conversion of rubusoside to stevioside is at least about 2% complete, as determined by any of the methods mentioned above. In a particular embodiment, the conversion of rubusoside to stevioside is at least about 10% complete, at least about 20% complete, at least about 30% complete, at least about 40% complete, at least about 50% complete, at least about 60% complete, at least about 70% complete, at least about 80% complete or at least about 90% complete. In a particular embodiment, the conversion of rubusoside to stevioside is at least about 95% complete.

The Conversion of Stevioside to Reb A

In one embodiment, a starting composition comprising stevioside is contacted with a UDP-glucosyltransferase capable of catalyzing the reaction of UDP-glucose and stevioside to produce reb A. Chemically, a glucose unit is added to the disaccharide at the C13 position of stevioside to provide reb A. In one embodiment, the starting composition comprises partially purified stevioside. In another embodiment, the starting composition comprises purified stevioside. In a particular embodiment, the starting composition comprises >99% stevioside. In a particular embodiment, the starting composition comprises greater than about 50%, about 60%, about 70% about 80% or about 90% stevioside.

In a particular embodiment, the UDP-glucosyltransferase is UGT76G1. UGT76G1 has been described by Richman et al. (Richman, A., Swanson, A., Humphrey, T., Chapman, R., McGarvey, B., Pocs, R., Brandle, J. Functional genomics uncovers three glucosyltransferases involved in the synthesis of the major sweet glucosides of *Stevia rebaudiana*. The Plant Journal, 2005, 41, 56-67) and is accessible in Genbank (ACT33422.1) and Uniprot (C7EA09). The enzyme was overexpressed in *E. coli* and was shown to transform stevioside to reb A.

In some embodiments, the UDP-glucosyltransferase, such as UGT76G1, can be prepared by expression in a host microorganism. Suitable host microorganisms include, but are not limited to, *E. coli, Saccharomyces* sp., *Aspergillus* sp., *Pichia* sp. In a particular embodiment, UGT76G1 is expressed in *E. coli*.

The UDP-glucosyltransferase, such as UGT76G1, can be free or immobilized. It can be in the form of crude, semi-purified and purified enzyme preparation(s). The UDP-glucosyltransferase can also be provided as a whole cell system, e.g., a living microbial cell, a whole microbial cell or cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of stevioside to reb A further comprising the addition of compounds other than UDP-glucose, stevioside and the UDP-glucosyltransferase. For example, in some embodiments, the reaction medium includes $MgCl_2$ and/or $MnCl_2$.

The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme sucrose synthase (FIG. 3). Stevioside is transformed into reb A with UDP-glucose which is recycled by the reaction between sucrose and UDP. As a consequence, stevioside and sucrose are used in stoichiometric amounts whereas UDP is present in catalytic amounts.

The reaction can be monitored by suitable method including, but not limited to, HPLC, LCMS, TLC, IR or NMR.

In one embodiment, the biocatalytic conversion or biotransformation of stevioside to reb A is at least about 50% complete, as determined by any of the methods mentioned above. In a particular embodiment, the conversion of stevioside to reb A is at least about 60% complete, at least about 70% complete, at least about 80% complete or at least about 90% complete. In a particular embodiment, the conversion of stevioside to reb A is at least about 95% complete.

The Conversion of Reb A to Reb D

In one embodiment, a starting composition comprising reb A is contacted with a UDP-glucosyltransferase capable of catalyzing the reaction of UDP-glucose and reb A to produce reb D. Chemically, a glucose unit is added to the monosaccharide at the C19 position of reb A to provide reb D. In one embodiment, the starting composition comprises partially purified reb A. In another embodiment, the starting composition comprises purified reb A. In a particular embodiment, the starting composition comprises >99% reb A. In a particular embodiment, the starting composition comprises greater than about 50%, about 60%, about 70% about 80% or about 90% reb A.

In a particular embodiment, the UDP-glucosyltransferase is UGT91D2, which has been described by Joseph et al. (Genbank accession no. ACE87855). It has to be noted that similar sequence was described later in a patent application PCT/US2011/038967 and named UGT91D2e. UGT91D2e shares >95% identity with UGT91D11 (Genbank accession no. AAR06918) and >99% identity with UGT of Joseph et al. (Genbank accession no. ACE87855).

In some embodiments, the UDP-glucosyltransferase, such as UGT91D2, is prepared by expression in a host microorganism. Suitable host microorganisms include, but are not limited to, *E. coli, Saccharomyces* sp., *Aspergillus* sp., *Pichia* sp. In a particular embodiment, UGT91D2 is expressed in *E. coli*.

The UDP-glucosyltransferase, such as UGT91D2, can be provided free or in an immobilized form. The enzyme preparation may be crude, semi-purified and purified. In one embodiment, the UDP-glucosyltransferase is provided as a whole-cell system, e.g., a living microbial cell, or whole microbial cells, cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of reb A to reb D further comprising the addition of compounds other than UDP-glucose, reb A and the UDP-glucosyltransferase. For example, in some embodiments, the reaction medium includes $MgCl_2$ and/or $MnCl_2$.

The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme sucrose synthase (FIG. 3). Reb A is transformed into reb D with UDP-glucose which is recycled by the reaction between sucrose and UDP. As a consequence, reb A and sucrose are used in stoichiometric amounts whereas UDP is present in catalytic amounts.

The reaction can be monitored by suitable method including, but not limited to, HPLC, LCMS, TLC, IR or NMR.

In one embodiment, the conversion of reb A to reb D is at least about 2% complete, as determined by any of the methods mentioned above. In a particular embodiment, the conversion of reb A to reb D is at least about 10% complete, at least about 20% complete, at least about 30% complete, at least about 40% complete, at least about 50% complete, at least about 60% complete, at least about 70% complete, at least about 80% complete or at least about 90% complete. In a particular embodiment, the conversion of reb A to reb D is at least about 95% complete.

The Conversion of Reb D to Reb X

In one embodiment, the starting composition comprises reb D, which is contacted with a UDP-glucosyltransferase capable of catalyzing the reaction of UDP-glucose and reb D to produce reb X. Chemically, a glucose unit is added to the disaccharide at the C19 position of reb D to provide reb X. In one embodiment, the starting composition comprises partially purified reb D. In another embodiment, the starting composition comprises purified reb D. In a particular embodiment, the starting composition comprises >99% reb D. In a particular embodiment, the starting composition comprises greater than about 50%, about 60%, about 70% about 80% or about 90% reb D. In a particular embodiment, the UDP-glucosyltransferase is UGT76G1.

In some embodiments, the UDP-glucosyltransferase, such as UGT91D2, can be prepared by expression in a host microorganism. Suitable host microorganisms include, but are not limited to, *E. coli, Saccharomyces* sp., *Aspergillus* sp., *Pichia* sp. In a particular embodiment, UGT91D2 is expressed in *E. coli*.

The UDP-glucosyltransferase, such as UGT91D2, can be provided as free or immobilized. The enzyme preparation can be crude, semi-purified and purified. In one embodiment, the UDP-glucosyltransferase is provided as a whole cell preparation, e.g., living microbial cells, or in the form of whole microbial cells, cell lysate and/or any other form of known in the art.

The reaction medium for conversion is generally aqueous, and can be purified water, buffer or a combination thereof. In a particular embodiment, the reaction medium is a buffer. Suitable buffers include, but are not limited to, PIPES buffer, acetate buffer and phosphate buffer. In one embodiment, the reaction medium is phosphate buffer.

In one embodiment, conversion of reb D to reb X employs compounds in addition to UDP-glucose, reb D and the UDP-glucosyltransferase. For example, in some embodiments, the reaction medium includes $MgCl_2$ and/or $MnCl_2$ The reaction can be carried out at temperature between about 0° C. and about 60° C., such as, for example, about 10° C., about 20° C., about 30° C., about 40° C., about 50° C. or about 60° C. In a particular embodiment, the reaction is carried out at about 30° C.

The reaction can proceed for a duration of time between 1 hour and 1 week, such as, for example, about 6 hours, about 12 hours, about 24 hours, about 48 hours, about 72 hours, about 120 hours, about 3 days, about 4 days, about 5 days, about 6 days or about 7 days. In a particular embodiment, the reaction is carried out for about 120 hours.

Optionally, the UDP-glucose, which is used as glucose donor, can be recycled by the use of the enzyme Sucrose Synthase (FIG. 3). Reb D is transformed into reb X with UDP-glucose which is recycled by the reaction between sucrose and UDP. As a consequence, reb D and sucrose are used in stoichiometric amounts whereas UDP is present in catalytic amounts.

The reaction can be monitored by suitable method including, but not limited to, HPLC, LCMS, TLC, IR or NMR.

In one embodiment, the conversion of reb D to reb X is at least about 50% complete, as determined by any of the methods mentioned above. In a particular embodiment, the conversion of reb D to reb X is at least about 60% complete, at least about 70% complete, at least about 80% complete or at least about 90% complete. In a particular embodiment, the conversion of reb D to reb X is at least about 95% complete.

The target steviol glycoside is optionally purified from the resulting composition. Purification of the target steviol glycoside from the reaction medium can be achieved by any suitable method to provide a highly purified target steviol glycoside composition. Suitable methods include crystallization, separation by membranes, centrifugation, extraction (liquid or solid phase), chromatographic separation, HPLC (preparative or analytical) or a combination of such methods.

In one embodiment, the particular biocatalytic conversion can be quenched to stop the reaction. The resultant mixture is then centrifuged. The supernatant generally contains the target steviol glycosides, and can then be further purified, if desired. For example, analytical or preparative HPLC can be used to separate remaining target or starting steviol glycoside(s) or reaction by-products from the target steviol glycoside. In one embodiment, separation is achieved with analytical HPLC. In another embodiment, separation is achieved with preparative HPLC. One of skill in the art will recognize that the particular HPLC method used can vary based on the particular system, solvent, and column. A suitable system for separating reb X from reb D is provided in the Example 20.

It is envisaged that the method provided herein can be repeated, wherein the composition resulting from the initial process, i.e., the composition comprising the target steviol glycoside, can then be used as the starting composition when the method is carried out a second time- or optionally, the target steviol glycoside can be purified from the composition comprising the target steviol glycoside to provide a highly purified target steviol glycoside or steviol glycoside composition. According to this embodiment, the target steviol glycoside produced when the method is carried out the first time can be considered a first target steviol glycoside or an intermediate target steviol glycoside, useful as a substrate for the production of a second target steviol glycoside, a second intermediate target steviol glycoside or an ultimate target steviol glycoside. The process can be repeated as many times as required to arrive at the ultimate target steviol glycoside. In one embodiment, the method is repeated once. In another embodiment, the method is repeated twice. In yet another embodiment, the method is repeated three times. In still other embodiments, the method is repeated four, five, six, seven, eight or nine times. On of skill in the art will recognize that the particular UDP-glucosyltransferase used in each reaction can either be the same or different, depending on the particular site on the steviol glycoside substrate where glucose is to be added.

Accordingly, in one embodiment, the method is repeated once, wherein the starting composition of the first method comprises reb A and the target steviol glycoside is reb D, and wherein starting composition of the second method comprises reb D and the target steviol glycoside is reb X.

In another embodiment, the method is repeated twice, wherein the starting composition of the first method comprises stevioside and the target steviol glycoside is reb A; the starting composition of the second method comprises reb A and the target steviol glycoside is reb D; and the starting composition of the third method comprises reb D and the target steviol glycoside is reb X.

In still another embodiment, the method is repeated three times, where the starting composition of the first method comprises rubusoside and the target steviol glycoside is stevioside; the starting composition of the second method comprises stevioside and the target steviol glycoside is reb A; the starting composition of the third method comprises reb A and the target steviol glycoside is reb D; and the starting composition of the fourth method comprises reb D and the target steviol glycoside is reb X In one embodiment, a method for producing a highly purified target steviol glycoside composition comprises:
  a. contacting a first starting composition comprising a steviol glycoside substrate with a first UDP-glucosyltransferase to produce a composition comprising a first target steviol glycoside;
  b. optionally separating the first target steviol glycoside from the medium to provide a highly purified first target steviol glycoside composition;
  c. contacting the composition comprising a first target steviol glycoside or the highly purified first target steviol glycoside composition with a second UDP-glucosyltransferase to produce a composition comprising a second target steviol glycoside:
  d. optionally separating the second target steviol glycoside from the medium to provide a highly purified second target steviol glycoside composition;
  e. contacting the composition comprising the second target steviol glycoside or the highly purified second target steviol glycoside composition with a third UDP-glucosyltransferase to produce a composition comprising a third target steviol glycoside; and
  f. optionally separating the third target steviol glycoside from the medium to provide a highly purified third target steviol glycoside composition.

In one embodiment, the first starting composition comprises stevioside, the first target steviol glycoside is reb A, and the first UDP-glucosyltransferase is UGT76G1.

In a further embodiment, the second UDP-glucosyltransferase is UGT91D2 and the second target steviol glycoside is reb D.

In a still further embodiment, the third UDP-glucosyltransferase is UGT91D2 and the third target steviol glycoside is reb X.

In one embodiment, one of more of the steps of contacting the composition comprising the steviol glycoside substrate with UDP-glucosyltransferase further includes providing a biocatalyst capable of UDP-overproduction and recycling and a substrate for said recycling.

In a more particular embodiment, a method for producing a highly purified target steviol glycoside composition comprises:
  a. contacting a first starting composition comprising a steviol glycoside substrate with a first UDP-glucosyltransferase to produce a composition comprising a first target steviol glycoside;
  b. optionally providing a biocatalyst capable of UDP-overproduction and recycling and a substrate for said recycling;
  c. optionally separating the first target steviol glycoside from the medium to provide a highly purified first target steviol glycoside composition;
  d. contacting the composition comprising a first target steviol glycoside or the highly purified first target steviol glycoside composition with a second UDP-glucosyltransferase to produce a composition comprising a second target steviol glycoside;
  e. optionally providing a biocatalyst capable of UDP-overproduction and recycling and a substrate for said recycling;
  f. optionally separating the second target steviol glycoside from the medium to provide a highly purified second target steviol glycoside composition;
  g. contacting the composition comprising the second target steviol glycoside or the highly purified second target steviol glycoside composition with a third UDP-glucosyltransferase to produce a composition comprising a third target steviol glycoside; and
  h. optionally separating the third target steviol glycoside from the medium to provide a highly purified third target steviol glycoside composition.

In one embodiment, the first starting composition comprises stevioside, the first target steviol glycoside is reb A, and the first UDP-glucosyltransferase is UGT76G1.

In a further embodiment, the second UDP-glucosyltransferase is UGT91D2 and the second target steviol glycoside is reb D.

In a still further embodiment, the third UDP-glucosyltransferase is UGT91D2 and the third target steviol glycoside is reb X In another particular embodiment, a method for producing a highly purified target steviol glycoside composition comprises:
  a. contacting a first starting composition comprising a steviol glycoside substrate with a first UDP-glucosyltransferase to produce a composition comprising a first target steviol glycoside;
  b. optionally providing a biocatalyst capable of UDP-overproduction and recycling and a substrate for said recycling;
  c. optionally separating the first target steviol glycoside from the medium to provide a highly purified first target steviol glycoside composition;
  d. contacting the composition comprising a first target steviol glycoside or the highly purified first target steviol glycoside composition with a second UDP-glucosyltransferase to produce a composition comprising a second target steviol glycoside;
  e. optionally providing a biocatalyst capable of UDP-overproduction and recycling and a substrate for said recycling;
  f. optionally separating the second target steviol glycoside from the medium to provide a highly purified second target steviol glycoside composition;
  g. contacting the composition comprising the second target steviol glycoside or the highly purified second target steviol glycoside composition with a third UDP-glucosyltransferase to produce a composition comprising a third target steviol glycoside; and
  h. optionally providing a biocatalyst capable of UDP-overproduction and recycling and a substrate for said recycling;
  i. optionally separating the third target steviol glycoside from the medium to provide a highly purified third target steviol glycoside composition;
  j. contacting the composition comprising the third target steviol glycoside or the highly purified third target steviol glycoside composition with a fourth UDP-glucosyltransferase to produce a composition comprising a fourth target steviol glycoside; and k. optionally providing a biocatalyst capable of UDP-overproduction and recycling and a substrate for said recycling;

l. optionally separating the fourth target steviol glycoside from the medium to provide a highly purified fourth target steviol glycoside composition.

In one embodiment, the first starting composition comprises rubusoside, the first target steviol glycoside is stevioside, and the first UDP-glucosyltransferase is UGT91D2.

In a further embodiment, the second UDP-glucosyltransferase is UGT76G1 and the second target steviol glycoside is reb A.

In a further embodiment, the third UDP-glucosyltransferase is UGT91D2 and the third target steviol glycoside is reb D.

In a still further embodiment, the fourth UDP-glucosyltransferase is UGT91D2 and the fourth target steviol glycoside is reb X.

Purified steviol glycosides, prepared in accordance with the present invention, may be used in a variety of products including, but not limited to, foods, beverages, pharmaceutical compositions, tobacco products, nutraceutical compositions, oral hygiene compositions, and cosmetic compositions.

Figure 4:
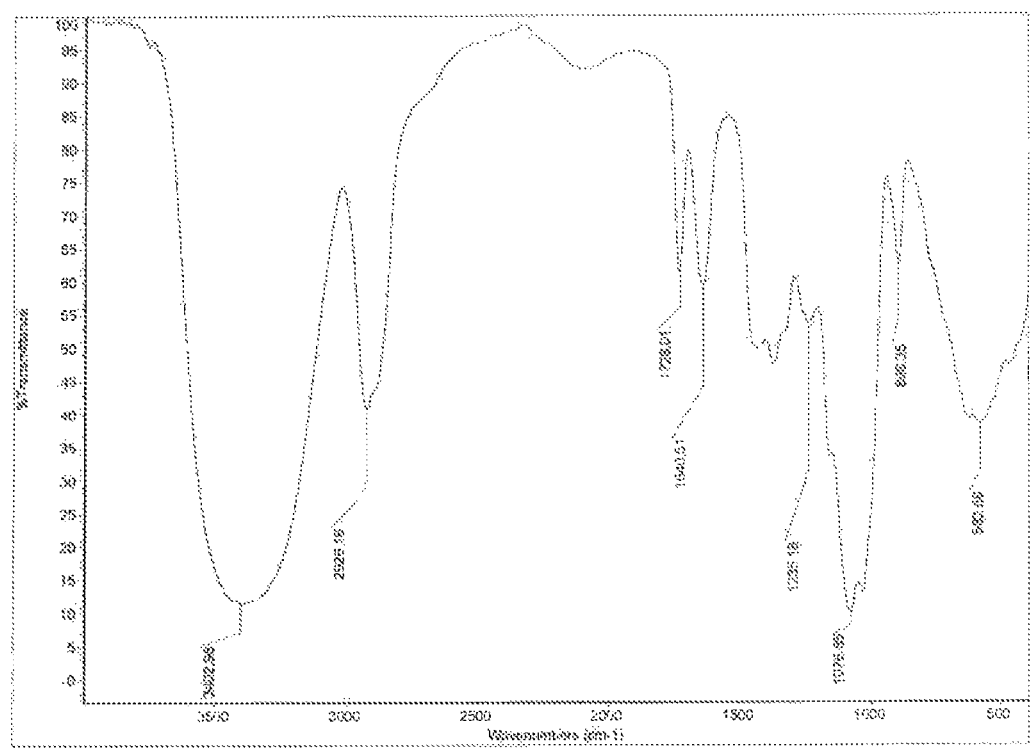
FIG. 4 shows the IR spectrum of reb X.

The high purity reb X obtained in this invention, having a molecular weight of 1291.29, a molecular formula of $C_{56}H_{90}O_{33}$, and the structure presented in FIG. 1, is in the form of a white and odorless powder. The compound is about 200 times sweeter than sugar when compared to a 10% sucrose solution. The infrared absorption spectrum is shown in FIG. 4.

Other properties of the pure reb X compound include a melting point of 249-250° C., and a specific rotation of $[\alpha]_D^{25}$ –19.00 in 50% ethanol (C=1.0). The solubility of reb X in water is around 0.3%, and increases with an increase in temperature.

Reb X is soluble in diluted solutions of methanol, ethanol, n-propanol, and isopropanol. However, it is insoluble in acetone, benzene, chloroform, and ether.

Reb X obtained in accordance with the present invention is heat and pH-stable.

Highly purified target glycoside(s) particularly, reb D and/or reb X obtained according to this invention can be used "as-is" or in combination with other sweeteners, flavors and food ingredients.

Non-limiting examples of flavors include lime, lemon, orange, fruit, banana, grape, pear, pineapple, mango, bitter almond, cola, cinnamon, sugar, cotton candy and vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners and gelling agents.

Highly purified target glycoside(s) particularly, reb D and/or reb X obtained according to this invention can be prepared in various polymorphic forms, including but not limited to hydrates, solvates, anhydrous, amorphous forms and/or mixtures thereof.

Highly purified target steviol glycoside(s), particularly, reb D and/or reb X obtained according to this invention may be incorporated as a high intensity natural sweetener in foodstuffs, beverages, pharmaceutical compositions, cosmetics, chewing gums, table top products, cereals, dairy products, toothpastes and other oral cavity compositions, etc.

Highly purified target steviol glycoside(s), particularly, reb D and/or reb X as a sweetening compound may be employed as the sole sweetener, or it may be used together with other naturally occurring high intensity sweeteners such as stevioside, reb A, reb B, reb C, reb D, reb E, reb F, steviolbioside, dulcoside A, rubusoside, mogrosides, brazzein, neohesperidin dihydrochalcone, glycyrrhizic acid and its salts, thaumatin, perillartine, pemrnandulcin, mukuroziosides, baiyunoside, phlomisoside-1, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, Luo Han Guo sweetener, mogroside V, siamenoside and others.

Highly purified target steviol glycoside(s), particularly, reb D and/or reb X may also be used in combination with synthetic high intensity sweeteners such as sucralose, potassium acesulfame, aspartame, alitame, saccharin, neohesperidin dihydrochalcone, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Moreover, highly purified target steviol glycoside(s), particularly, reb D and/or reb X can be used in combination with natural sweetener suppressors such as gymnemic acid, hodulcin, ziziphin, lactisole, and others. Reb D and/or reb X may also be combined with various umami taste enhancers. Reb D and/or reb X can be mixed with umami tasting and sweet aminoacids such as glutamate, aspartic acid, glycine, alanine, threonine, proline, serine, glutamate, and tryptophan.

Highly purified target steviol glycoside(s), particularly, reb D and/or reb X may also be combined with polyols or sugar alcohols. The term "polyol" refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Examples of polyols include, but are not limited to, erythritol, maltitol, mannitol, sorbitol, lactitol, xylitol, inositol, isomalt, propylene glycol, glycerol, threitol, galactitol, hydrogenated isomaltulose, reduced isomalto-oligosaccharides, reduced xylo-oligosaccharides, reduced gentio-oligosaccharides, reduced maltose syrup, reduced glucose syrup, hydrogenated starch hydrolyzates, polyglycitols and sugar alcohols or any other carbohydrates capable of being reduced which do not adversely affect the taste of the sweetener composition.

Highly purified target steviol glycoside(s), particularly, reb D and/or reb A may be combined with reduced calorie sweeteners such as D-tagatose, L-sugars, L-sorbose, L-arabinose, and others.

Highly purified target steviol glycoside(s), particularly, reb D and/or reb X may also be combined with various carbohydrates. The term "carbohydrate" generally refers to aldehyde or ketone compounds substituted with multiple hydroxyl groups, of the general formula $(CH_2O)_n$, wherein n is 3-30, as well as their oligomers and polymers. The carbohydrates of the present invention can, in addition, be substituted or deoxygenated at one or more positions. Carbohydrates, as used herein, encompass unmodified carbohydrates, carbohydrate derivatives, substituted carbohydrates, and modified carbohydrates. As used herein, the phrases "carbohydrate derivatives", "substituted carbohydrate", and "modified carbohydrates" are synonymous. Modified carbohydrate means any carbohydrate wherein at least one atom has been added, removed, or substituted, or combinations thereof. Thus, carbohydrate derivatives or substituted carbohydrates include substituted and unsubstituted monosaccharides, disaccharides, oligosaccharides, and polysaccharides. The carbohydrate derivatives or substituted carbohydrates optionally can be deoxygenated at any corresponding C-position, and/or substituted with one or more moieties such as hydrogen, halogen, haloalkyl, carboxyl, acyl, acyloxy, amino, amido, carboxyl derivatives, alkylamino, dialkylamino, arylamino, alkoxy, aryloxy, nitro, cyano, sulfo, mercapto, imino, sulfonyl, sulfenyl, sulfinyl, sulfamoyl, carboalkoxy, carboxamido, phosphonyl, phosphinyl, phosphoryl, phosphino, thioester, thioether, oximino, hydrazino, carbamyl, phospho, phosphonato, or any other viable functional group provided the carbohydrate derivative or substituted carbohydrate functions to improve the sweet taste of the sweetener composition.

Examples of carbohydrates which may be used in accordance with this invention include, but are not limited to, tagatose, trehalose, galactose, rhamnose, various cyclodextrins, cyclic oligosaccharides, various types of maltodextrins, dextran, sucrose, glucose, ribulose, fructose, threose, arabinose, xylose, lyxose, allose, altrose, mannose, idose, lactose, maltose, invert sugar, isotrehalose, neotrehalose, isomaltulose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), xylo-terminated oligosaccharides, gentio-oligosaccharides (gentiobiose, gentiotriose, gentiotetraose and the like), sorbose, nigero-oligosaccharides, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), starch, inulin, inulo-oligosaccharides, lactulose, melibiose, raffinose, ribose, isomerized liquid sugars such as high fructose corn syrups, coupling sugars, and soybean oligosaccharides. Additionally, the carbohydrates as used herein may be in either the D- or L-configuration.

Highly purified target steviol glycoside(s), particularly, reb D and/or reb X obtained according to this invention can be used in combination with various physiologically active substances or functional ingredients. Functional ingredients generally are classified into categories such as carotenoids, dietary fiber, fatty acids, saponins, antioxidants, nutraceuticals, flavonoids, isothiocyanates, phenols, plant sterols and stanols (phytosterols and phytostanols); polyols; prebiotics, probiotics; phytoestrogens; soy protein; sulfides/thiols; amino acids; proteins; vitamins; and minerals. Functional ingredients also may be classified based on their health benefits, such as cardiovascular, cholesterol-reducing, and anti-inflammatory.

Highly purified target steviol glycoside(s), particularly, reb D and/or reb X obtained according to this invention may be applied as a high intensity sweetener to produce zero calorie, reduced calorie or diabetic beverages and food products with improved taste characteristics. It may also be used in drinks, foodstuffs, pharmaceuticals, and other products in which sugar cannot be used. In addition, highly purified target steviol glycoside(s), particularly, reb D and/or reb X can be used as a sweetener not only for drinks, foodstuffs, and other products dedicated for human consumption, but also in animal feed and fodder with improved characteristics.

Examples of products in which highly purified target steviol glycoside(s), particularly, reb D and/or reb X may be used as a sweetening compound include, but are not limited to, alcoholic beverages such as vodka, wine, beer, liquor, and sake, etc.; natural juices; refreshing drinks; carbonated soft drinks; diet drinks; zero calorie drinks; reduced calorie drinks and foods; yogurt drinks; instant juices; instant coffee; powdered types of instant beverages; canned products; syrups; fermented soybean paste; soy sauce; vinegar; dressings; mayonnaise; ketchups; curry; soup; instant bouillon; powdered soy sauce; powdered vinegar; types of biscuits; rice biscuit; crackers; bread; chocolates; caramel; candy; chewing gum; jelly; pudding; preserved fruits and vegetables; fresh cream; jam; marmalade; flower paste; powdered milk; ice cream; sorbet; vegetables and fruits packed in bottles; canned and boiled beans; meat and foods boiled in sweetened sauce; agricultural vegetable food products; seafood; ham; sausage; fish ham; fish sausage; fish paste; deep fried fish products; dried seafood products; frozen food products; preserved seaweed; preserved meat; tobacco; medicinal products; and many others. In principle it can have unlimited applications.

During the manufacturing of products such as foodstuffs, drinks, pharmaceuticals, cosmetics, table top products, and chewing gum, the conventional methods such as mixing, kneading, dissolution, pickling, permeation, percolation, sprinkling, atomizing, infusing and other methods may be used.

Moreover, the highly purified target steviol glycoside(s), particularly, reb D and/or reb X obtained in this invention may be used in dry or liquid forms. It can be added before or after heat treatment of food products. The amount of the highly purified target steviol glycoside(s), particularly, reb D and/or reb X depends on the purpose of usage. As discussed above, it can be added alone or in combination with other compounds.

The following examples illustrate preferred embodiments of the invention for the preparation of highly purified target steviol glycoside(s), particularly, reb D and/or reb X. It will be understood that the invention is not limited to the materials, proportions, conditions and procedures set forth in the examples, which are only illustrative.

EXAMPLE 1

In-vivo Production of UGT76G1

NcoI and NdeI restriction sides were added to the original nucleic sequence as described in Genbank accession no. AAR006912.1. After codon optimization the following nucleic sequence (SEQ ID NO. 1) was obtained:

Sequence Listing Free Text

```
CCATGGCCCATATGGAAAACAAAACCGAAACCACCGTTCGTCGTCGTCGC
CGTATTATTCTGTTTCCGGTTCCGTTTCAGGGTCATATTAATCCGATTCT
GCAGCTGGCAAATGTGCTGTATAGCAAAGGTTTTAGCATTACCATTTTTC
ATACCAATTTTAACAAACCGAAAACCAGCAATTATCCGCATTTTACCTTT
CGCTTTATTCTGGATAATGATCCGCAGGATGAACGCATTAGCAATCTGCC
GACACATGGTCCGCTGGCAGGTATGCGTATTCCGATTATTAACGAACATG
GTGCAGATGAACTGCGTCGTGAACTGGAACTGCTGATGCTGGCAAGCGAA
GAAGATGAAGAAGTTAGCTGTCTGATTACCGATGCACTGTGGTATTTTGC
ACAGAGCGTTGCAGATAGCCTGAATCTGCGTCGTCTGGTTCTGATGACCA
GCAGCCTGTTTAACTTTCATGCACATGTTAGCCTGCCGCAGTTTGATGAA
CTGGGTTATCTGGATCCGGATGATAAAACCCGTCTGGAAGAACAGGCAAG
CGGTTTTCCGATGCTGAAAGTGAAAGATATCAAAAGCGCCTATAGCAATT
GGCAGATTCTGAAAGAAATTCTGGGCAAAATGATTAAACAGACCAAAGCA
AGCAGCGGTGTTATTTGGAATAGCTTTAAAGAACTGGAAGAAAGCGAACT
GGAAACCGTGATTCGTGAAATTCCGGCACCGAGCTTTCTGATTCCGCTGC
CGAAACATCTGACCGCAAGCAGCAGCAGCCTGCTGGATCATGATCGTACC
GTTTTTCAGTGGCTGGATCAGCAGCCTCCGAGCAGCGTTCTGTATGTTAG
CTTTGGTAGCACCAGCGAAGTTGATGAAAGATTTTCTGGAAATTGCCCGT
GGTCTGGTTGATAGCAAACAGAGCTTTCTGTGGGTTGTTCGTCCGGGTTT
TGTTAAAGGTAGCACCTGGGTTGAACCGCTGCCGGATGGTTTTCTGGGTG
AACGTGGTCGTATTGTTAAATGGGTTCCGCAGCAAGAAGTTCTGGCACAC
GGCGCAATTGGTGCATTTTGGACCCATAGCGGTTGGAATAGCACCCTGGA
AAGCGTTTGTGAAGGTGTTCCGATGATTTTTAGCGATTTTGGTCTGGATC
AGCCGCTGAATGCACGTTATATGAGTGATGTTCTGAAAGTGGGTGTGTAT
CTGGAAAATGGTTGGGAACGTGGTGAAATTGCAAATGCAATTCGTCGTGT
TATGGTGGATGAAGAAGGTGAATATATTCGTCAGAATGCCCGTGTTCTGA
AACAGAAAGCAGATGTTAGCCTGATGAAAGGTGGTAGCAGCTATGAAAGC
CTGGAAAGTCTGGTTAGCTATATTAGCAGCCTGTAATAACTCGAG
```

After synthesis of the gene and subcloning into pET30A+ vector using NdeI and XhoI cloning sites, the UGT76G1_pET30a+ plasmid was introduced in E. coli Bl21(DE3) and E. coli EC100 by electroporation. The obtained cells were grown in petri-dishes in the presence of Kanamycin and suitable colonies were selected and allowed to grow in liquid LB medium (erlenmeyer flasks). Glycerol was added to the suspension as cryoprotectant and 400 µL aliquots were stored at −20° C. and at −80° C.

The storage aliquots of E. coli BL21(DE3) containing the pET30A+_UGT76G1 plasmid were thawed and added to 30 mL of LBGKP medium (20 g/L Luria Broth Lennox; 50 mM PIPES buffer pH 7.00; 50 mM Phosphate buffer pH 7.00; 2.5 g/L glucose and 50 mg/L of Kanamycin). This culture was allowed to shake at 135 rpm at 30° C. for 8 h.

The production medium contained 60 g/L of overnight express instant TB medium (Novagen), 10 g/L of glycerol and 50 mg/L of Kanamycin. The medium was allowed to stir at 20° C. while taking samples to measure the OD and pH.

The cultures gave significant growth and a good OD was obtained. After 40 h, the cells were harvested by centrifugation and frozen to yield 12.7 g of cell wet weight.

Lysis was performed by addition of Bugbuster Master mix (Novagen) and the lysate was recovered by centrifugation and kept frozen. Activity tests were performed with thawed lysate.

EXAMPLE 2

In-vitro Production of UGT76G1

The S30 T7 High Yield Protein expression system kit from Promega was used. 4 µg of UGT76G1_pET30a+ plasmid from E. coli EC100 was mixed with 80 µL of S30 premix plus and 72 µL of S30 T7 extract was added. Nuclease-free water was added in order to obtain a total volume of 200 µL and the resulting solution was incubated for 2 h at 30° C. 180 µL was used in the catalytic test reaction.

EXAMPLE 3

In-vitro Production of UGT91D2

NcoI and NdeI restriction sides were added to the original nucleic sequence as described in Genbank accession no. ACE87855.1. After codon optimization the following nucleic sequence (SEQ ID NO. 2) was obtained:

Sequence Listing Free Text

```
CCATGGCACATATGGCAACCAGCGATAGCATTGTTGATGATCGTAAACAG
CTGCATGTTGCAACCTTTCCGTGGCTGGCATTTGGTCATATTCTGCCGTA
TCTGCAGCTGAGCAAACTGATTGCAGAAAAAGGTCATAAAGTGAGCTTTC
TGAGCACCACCCGTAATATTCAGCGTCTGAGCAGCCATATTAGTCCGCTG
ATTAATGTTGTTCAGCTGACCCTGCCTCGTGTTCAAGAACTGCCGGAAGA
TGCCGAAGCAACCACCGATGTTCATCCGGAAGATATTCCGTATCTGAAAA
AAGCAAGTGATGGTCTGCAGCCGGAAGTTACCCGTTTTCTGGAACAGCAT
AGTCCGGATTGGATCATCTATGATTATACCCATTATTGGCTGCCGAGCAT
TGCAGCAAGCCTGGGTATTAGCCGTGCACATTTTAGCGTTACCACCCCGT
GGGCAATTGCATATATGGGTCCGAGCGCAGATGCAATGATTAATGGTAGT
GATGGTCGTACCACCGTTGAAGATCTGACCACCCCTCCGAAATGGTTTCC
GTTTCCGACCAAAGTTTGTTGGCGTAAACATGATCTGGCACGTCTGGTTC
CGTATAAAGCACCGGGTATTAGTGATGGTTATCGTATGGGTCTGGTTCTG
AAAGGTAGCGATTGTCTGCTGAGCAAATGCTATCATGAATTTGGCACCCA
GTGGCTGCCGCTGCTGGAAACCCTGCATCAGGTTCCGGTTGTTCCGGTGG
GTCTGCTGCCTCCGGAAGTTCCGGGTGATGAAAAAGATGAAACCTGGGTT
AGCATCAAAAAATGGCTGGATGGTAAACAGAAAGGTAGCGTGGTTTATGT
TGCACTGGGTAGCGAAGTTCTGGTTAGCCAGACCGAAGTTGTTGAACTGG
CACTGGGTCTGGAACTGAGCGGTCTGCCGTTTGTTTGGGCATATCGTAAA
CCGAAAGGTCCGGCAAAAAGCGATAGCGTTGAACTGCCGGATGGTTTTGT
TGAACGTACCCGTGATCGTGGTCTGGTTTGGACCAGCTGGGCACCTCAGC
```

-continued

```
TGCGTATTCTGAGCCATGAAAGCGTTTGTGGTTTTCTGACCCATTGTGGT

AGCGGTAGCATTGTGGAAGGTCTGATGTTTGGTCATCCGCTGATTATGCT

GCCGATTTTTGGTGATCAGCCGCTGAATGCACGTCTGCTGGAAGATAAAC

AGGTTGGTATTGAAATTCCGCGTAATGAAGAAGATGGTTGCCTGACCAAA

GAAAGCGTTGCACGTAGCCTGCGTAGCGTTGTTGTTGAAAAAGAAGGCGA

AATCTATAAAGCCAATGCACGTGAACTGAGCAAAATCTATAATGATACCA

AAGTGGAAAAAGAATATGTGAGCCAGTTCGTGGATTATCTGGAAAAAAAC

ACCCGTGCAGTTGCCATTGATCACGAAAGCTAATGACTCGAG
```

After synthesis of the gene and subcloning into pET30A+ vector using NcoI and XhoI cloning sites, the UGT91D2_pET30a+ plasmid was introduced into *E. coli* EC100 by electroporation. The obtained cells were grown in the presence of Kanamycin and suitable colonies were selected and allowed to grow in liquid LB medium (erlenmeyer flasks). Glycerol was added to the suspension as cryoprotectant and 400 µL aliquots were stored at −20° C. and at −80° C.

The S30 T7 High Yield Protein expression system kit from Promega was used for the in-vitro synthesis of the protein.

4 µg of UGT91D2_pET30a+ plasmid was mixed with 80 µL of S30 premix plus and 72 µL of S30 T7 extract was added. Nuclease-free water was added in order to obtain a total volume of 200 µL and the resulting solution was incubated for 2 h at 30° C. 5 µL was used for SDS-page analysis while the remaining 45 µL was used in the catalytic test reaction.

EXAMPLE 4

Catalytic Reaction with In-vivo Produced UGT76G1

The total volume of the reaction was 5.0 mL with the following composition: 50 mM sodium phosphate buffer pH 7.2, 3 mM $MgCl_2$, 2.5 mM UDP-glucose, 0.5 mM Stevioside and 500 µL of UGT76G1 thawed lysate. The reactions were run at 30° C. on an orbitary shaker at 135 rpm. For each sample, 460 µL of the reaction mixture was quenched with 40 µL of 2N $H_2SO_4$ and 420 µL of methanol/water (6/4). The samples were immediately centrifuged and kept at 10° C. before analysis by HPLC (CAD). HPLC indicated almost complete conversion of stevioside to rebaudioside A.

EXAMPLE 5

Catalytic Reaction with In-vitro Produced UGT91D2

The total volume of the reaction was 0.5 mL with the following composition: 50 mM sodium phosphate buffer pH 7.2, 3 mM $MgCl_2$, 3.8 mM UDP-glucose, 0.1 mM Rebaudioside A and 180 µL of in-vitro produced UGT91D2. The reactions were run at 30° C. on an orbitary shaker at 135 rpm. For each sample, 450 µL of reaction mixture was quenched with 45 µL of 2N $H_2SO_4$ and 405 µL of 60% MeOH. After centrifugation, the supernatant was analyzed by HPLC (CAD). HPLC indicated a 4.7% conversion of rebaudioside A to rebaudioside D after 120 h.

EXAMPLE 6

Catalytic Reaction with In-vitro Produced UGT76G1

The total volume of the reaction was 2 mL with the following composition: 50 mM sodium phosphate buffer pH 7.2, 3 mM $MgCl_2$, 3.8 mM UDP-glucose, 0.5 mM Rebaudioside D and 180 µL of in-vitro produced UGT76G1. The reactions were run at 30° C. on an orbitary shaker at 135 rpm. For each sample, 400 µL of reaction mixture was quenched with 40 µL of 2N $H_2SO_4$ and 360 µL of 60% MeOH. After centrifugation, the supernatant was analyzed by HPLC (CAD). HPLC indicated 80% conversion of rebaudioside D to rebaudioside X after 120 h.

For examples 7 to 12, the following abbreviations were used:

LBGKP medium: 20 g/L Luria Broth Lennox; 50 mM PIPES buffer pH 7.00; 50 mM Phosphate buffer pH 7.00; 2.5 g/L glucose and 50 mg/L of Kanamycin or Ampicillin LB medium: (20 g/L Luria Broth Lennox)

EXAMPLE 7

Preparation and Activity of UGT76G1 Prepared by pET30a+ Plasmid and BL21 (DE3) Expression Strain The pET30a+_UGT76G1 plasmid was transformed into BL21(DE3) expression strain (Lucigen E. Cloni® EXPRESS Electrocompetent Cells). The obtained cells were grown on LB Agar medium in petri-dishes in the presence of Kanamycin. Suitable colonies were selected and allowed to grow in liquid LBGKP medium containing Kanamycin. Glycerol was added and 400 µL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 20° C. while taking samples to measure the OD (600 nm) and pH. After 40 h, the cells were harvested by centrifugation and frozen. The obtained cell wet weight was 10.58 g.

3.24 g of obtained pellet was lysed by addition of 8.1 mL of "Bugbuster Master mix" (Novagen, reference 71456) and 3.5 mL of water. The lysate was recovered by centrifugation and kept frozen.

EXAMPLE 8

Preparation and Activity of UGT76G1 Prepared by pET30a+ Plasmid and Tuner (DE3) Expression Strain The pET30a+_UGT76G1 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium containing Kanamycin). Glycerol was added and 400 µL aliquots were stored at −20° C. and at −80° C.

A storage aliquot was thawed and added to 100 mL of LB medium containing 50 mg/L of Kanamycin. This culture allowed to shake at 30° C. for 15 h. 4.4 mL of this culture was used to inoculate 200 mL of production medium containing LB. This medium was allowed to stir at 37° C. until an OD (600 nm) of 0.9 was obtained, after which 400 μL of a 100 mM IPTG solution was added and the medium was allowed to stir at 30° C. for 4 h. The cells were harvested by centrifugation and frozen. The obtained cell wet weight was 1.38 g.

The obtained pellet was lysed by addition of 4.9 mL of "Bugbuster Master mix" (Novagen, reference 71456) and 2.1 mL of water. The lysate was recovered by centrifugation and kept frozen.

EXAMPLE 9

Preparation and Activity of UGT76G1 Prepared by pMAL Plasmid and BL21 Expression Strain After subcloning the synthetic UGT76G1 gene into the pMAL plasmid using NdeI and SalI cloning sites, the pMAL_UGT76G1 plasmid was transformed into BL21 expression strain (New England Biolabs BL21 Competent *E. coli*) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 μL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight was 5.86 g.

2.74 g of obtained pellet was lysed by addition of 9.6 mL of "Bugbuster Master Mix" (Novagen, reference 71456) and 4.1 mL of water. The lysate was recovered by centrifugation and kept frozen.

EXAMPLE 10

Preparation and Activity of UGT76G1 Prepared by pMAL Plasmid and ArcticExpress Expression Strain The pMAL_UGT76G1 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing of Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 12° C. while taking samples to measure the OD (600 nm) and pH. After 68 h, the cells were harvested by centrifugation and frozen. The obtained cell wet weight was 8.96 g.

2.47 g of the obtained pellet was lysed by addition of 8.73 mL of "Bugbuster Master Mix" (Novagen, reference 71456) and 3.79 mL of water. The lysate was recovered by centrifugation and kept frozen.

EXAMPLE 11

Preparation and Activity of UGT76G1 Prepared by pCOLDIII Plasmid and ArcticExpress Expression Strain After subcloning the synthetic UGT76G1 gene into the pCOLDIII plasmid using NdeI and XhoI cloning sites, the pCOLDIII_UGT76G1 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 μL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 63 h, the cells were harvested by centrifugation and frozen. The obtained cell wet weight was 6.54 g.

2.81 g of the obtained pellet was lysed by addition of 9.8 mL of "Bugbuster Master Mix" (Novagen, reference 71456) and 4.2 mL of water. The lysate was recovered by centrifugation and kept frozen.

EXAMPLE 12

Preparation and Activity of UGT76G1 Prepared by pCOLDIII Plasmid and Origami2 (DE3) Expression Strain The pCOLDIII_UGT76G1 plasmid was transformed into Origami2 (DE3) expression strain (Novagen Origami™2 (DE3) Competent Cells) by heat shock treatment. The obtained cells were grown on LB Agar medium in petri-dishes in the presence of Ampicillin. Suitable colonies were selected and allowed to grow in liquid LBGKP medium containing Ampicillin. Glycerol was added and 400 μL aliquots were stored at −20° C. and at −80° C.

A storage aliquot was thawed and added to 30 mL of LBGKP medium (containing Ampicillin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Kanamycin. The medium was allowed to stir at 12° C. while taking samples to measure the OD (600 nm) and pH. After 68 h, the cells were harvested by centrifugation and frozen. The obtained cell wet weight was 2.53 g.

1.71 g of the obtained pellet was lysed by addition of 6.0 mL of "Bugbuster Master mix" (Novagen, reference 71456) and 1.9 mL of water. The lysate was recovered by centrifugation and kept frozen.

EXAMPLE 13

Determination of Activity

Activity tests were performed on a 5 mL scale with 500 µL of thawed lysate for the transformation of Stevioside to Rebaudioside A and Rebaudioside D to Rebaudioside X using 0.5 mM of substrate, 2.5 mM of UDP-Glucose and 3 mM $MgCl_2$ in 50 mM Sodium Phosphate buffer at pH 7.2. Samples were taken and analyzed by HPLC. The results for the different preparations of UGT76G1 are summarized in the following table.

|  |  |  | Transformation activity* | |
|---|---|---|---|---|
| Example | Plasmid | Expression strain | Stevioside to Rebaudioside A | Rebaudioside D to Rebaudioside X |
| 7 | pET30a+ | BL21 (DE3) | 29 U mL$^{-1}$ | 0.31 U mL$^{-1}$ |
| 8 | pET30a+ | Tuner (DE3) | 33 U mL$^{-1}$ | 0.40 U mL$^{-1}$ |
| 9 | pMAL | BL21 | 20 U mL$^{-1}$ | 0.15 U mL$^{-1}$ |
| 10 | pMAL | ArcticExpress | 15 U mL$^{-1}$ | 0.25 U mL$^{-1}$ |
| 11 | pCOLDIII | ArcticExpress | 15 U mL$^{-1}$ | 0.11 U mL$^{-1}$ |
| 12 | pCOLDIII | Origami2 (DE3) | 37 U mL$^{-1}$ | 0.20 U mL$^{-1}$ |

*Note
The activities for the transformation of Stevioside and Rebaudioside X are mentioned per mL of lysate. 1 U will transform 1 µmol of substrate in 1 hour at 30° C. and pH 7.2

EXAMPLE 14

50 mL Scale Reaction for the Transformation of Rebaudioside D to Rebaudioside X 5 mL of the lysate of Example 12 was used to transform Rebaudioside D to Rebaudioside X on a 50 mL scale. The reaction medium consisted of 50 mM Sodium Phosphate buffer pH 7.2, 3 mM of $MgCl_2$, 2.5 mM of UDP-Glucose and 0.5 mM of Rebaudioside D. After allowing the reaction to be shaken at 30° C. for 90 h. 50 mL of ethanol was added and the resulting mixture was allowed to stir at −20° C. for 1 h. After centrifugation at 5000 g for 10 min. the supernatant was purified via ultrafiltration (Vivaflow MWCO 30000). 78 mL of permeate was obtained and the 9 mL of retentate was diluted with 9 mL of ethanol and resubjected to Ultrafiltration (Vivaflow MWCO 30000). Another 14 mL of filtrate was obtained, which was combined with the first permeate. The combined permeates were concentrated under reduced pressure at 30° C. until 32 mL of a clear solution was obtained.

Figure 5:
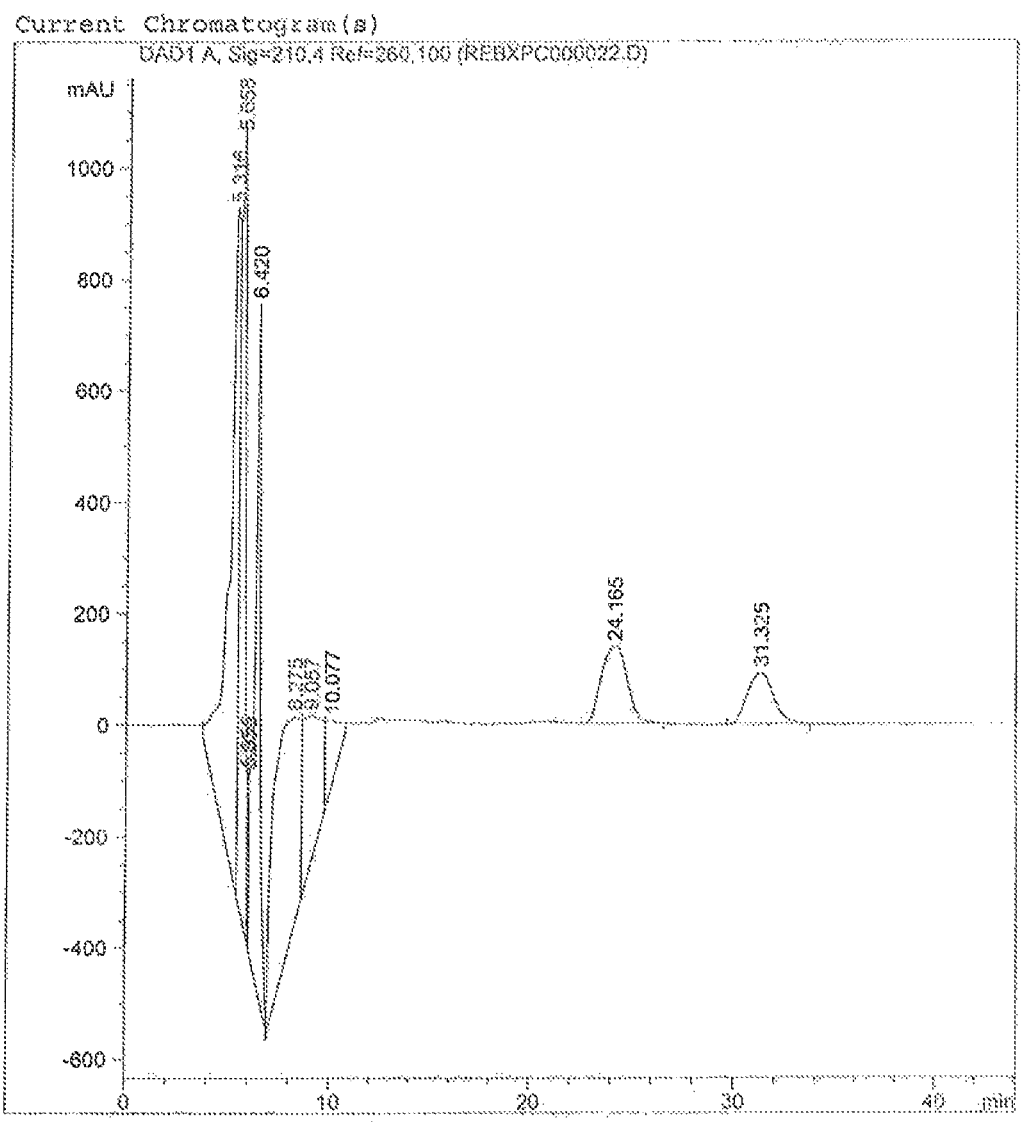
FIG. 5. shows the HPLC chromatogram of the product of the biocatalytic production of reb X from reb D, as detailed in Example 14. The peak with retention time of 24.165 minutes corresponds to unreacted reb D. The peak with retention time of 31.325 minutes corresponds to reb X.

The HPLC trace of the product mixture is shown in FIG. 5. HPLC was carried out on an Agilent 1200 series equipped with a binary pump, auto sampler, and thermostat column compartment. The method was isocratic, with a mobile phase composed of 70% water (0.1% formic acid):30% acetonitrile. The flow rate was 0.1 µL/min. The column used was Phenomenex Prodigy 5µ ODS (3) 100 A; 250×2 mm. The column temperature was maintained at 40° C. The injection volume was 20-40 µl.

EXAMPLE 15

Preparation of UGT91D2 Using pMAL Plasmid and BL21 Expression Strain

After subcloning the synthetic UGT91D2 gene into the pMAL plasmid using NdeI and SalI cloning sites, the pMAL_UGT91D2 plasmid was transformed into BL21 expression strain (New England Biolabs BL21 Competent E. coli) by heat shock treatment. The obtained cells were grown on LB Agar medium in petri-dishes in the presence of Ampicillin. Suitable colonies were selected and allowed to grow in liquid LBGKP medium containing Ampicillin). Glycerol was added and 400 µL aliquots were stored at −20° C. and at −80° C.

A storage aliquot was thawed and added to 30 mL of LBGKP medium. This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. while taking samples to measure the OD and pH. After 40 h, the cells were harvested by centrifugation and frozen. The obtained cell wet weight is 12.32 g.

2.18 g of obtained pellet was lysed by addition of 7.7 mL of "Bugbuster Master Mix" (Novagen, reference 71456) and 3.2 mL of water. The lysate was recovered by centrifugation and used directly for activity testing.

EXAMPLE 16

Preparation of UGT91D2 Using pMAL Plasmid and ArcticExpress Expression Strain The pMAL_UGT91D2 plasmid was transformed into ArcticExpress expression strain (Agilent ArcticExpress competent cells) by heat shock treatment. The obtained cells were grown on LB Agar medium in petri-dishes in the presence of Ampicillin and Geneticin. Suitable colonies were selected and allowed to grow in liquid LBGKP medium containing Ampicillin and Geneticin. Glycerol was added and 400 µL aliquots were stored at −20° C. and at −80° C.

A storage aliquot was thawed and added to 30 mL of LBGKP medium (containing Ampicillin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. The cells were harvested by centrifugation and frozen. The obtained cell wet weight is 15.77 g.

2.57 g of the obtained pellet was lysed by addition of 9.0 mL of "Bugbuster Master Mix" (Novagen, reference 71456) and 3.8 mL of water. The lysate was recovered by centrifugation and used directly for activity testing.

EXAMPLE 17

Preparation of UGT91D2 Using pET30a+ Plasmid and Tuner (DE3) Expression Strain The pET30a+_UGT91D2 plasmid was transformed into Tuner (DE3) expression strain (Novagen Tuner™ (DE3) Competent cells) by heat shock treatment. The obtained cells were grown on LB Agar medium in petri-dishes in the presence of Kanamycin. Suitable colonies were selected and allowed to grow in liquid LBGKP medium (containing Kanamycin). Glycerol was added and 400 µL aliquots were stored at −20° C. and at −80° C.

A storage aliquot was thawed and added to 100 mL of LB medium containing 50 mg/L of Kanamycin. This culture allowed to shake at 30° C. for 15 h. 6.2 mL of this culture was used to inoculate 500 mL of production medium containing LB. This medium was allowed to stir at 37° C. until an OD (600 nm) of 0.9 was obtained after which 500 µL of a 100 mM IPTG solution was added (IPTG concentration in medium is 100 µM) and the medium was allowed to stir at 30° C. for 4 h, the cells were harvested by centrifugation and frozen. The obtained cell wet weight is 4.02 g.

1.92 g of the obtained pellet was lysed by addition of 6.8 mL of "Bugbuster Master mix" (Novagen, reference 71456) and 2.8 mL of water. The lysate was recovered by centrifugation and tested directly for activity.

EXAMPLE 18

Preparation of UGT91D2 Using pET30a+ Plasmid and ArcticExpress Expression Strain The pET30a+_UGT91D2 plasmid was transformed into ArcticExpress (DE3) expression strain (Agilent ArcticExpress competent cells) by heat shock treatment. The obtained cells were grown on LB Agar medium in petri-dishes in the presence of Kanamycin and Geneticin. Suitable colonies were selected and allowed to grow in liquid LBGKP medium containing of Kanamycin and Geneticin. Glycerol was added and 400 µL aliquots were stored at −20° C. and at −80° C.

A storage aliquot was thawed and added to 30 mL of LBGKP medium (containing Kanamycin and Geneticin). This culture was allowed to shake at 30° C. for 8 h. and subsequently used to inoculate 400 mL of production medium containing 60 g/L of "Overnight express instant TB medium" (Novagen, reference 71491-5), 10 g/L of glycerol and 50 mg/L of Ampicillin. The medium was allowed to stir at 20° C. for 16 h. followed by another 50 h. at 12° C. while taking samples to measure the OD (600 nm) and pH. After 60 h, the cells were harvested by centrifugation and frozen. The obtained cell wet weight is 16.07 g.

3.24 g of the obtained pellet was lysed by addition of 11.4 mL of "Bugbuster Master Mix" (Novagen, reference 71456) and 4.8 mL of water. The lysate was recovered by centrifugation and used directly for activity testing.

EXAMPLE 19

Determination of Activity of In-Vivo Preparations of UGT91D2

Activity tests were performed at 5 mL scale with 1000 µL of lysate for the transformation of Rubusoside to Stevioside using 0.5 mM of substrate, 2.5 mM of UDP-Glucose and 3 mM $MgCl_2$ in 50 mM Sodium Phosphate buffer at pH 7.2.

Samples were taken and analyzed by HPLC. The results for the different preparations of UGT91D2 are summarized in the following table.

| Example | Plasmid | Expression strain | Transformation activity* Rubusoside to Stevioside |
|---|---|---|---|
| 15 | pMAL | BL21 | 9 mU mL$^{-1}$ |
| 16 | pMAL | ArcticExpress | 60 mU mL$^{-1}$ |
| 17 | pET30a+ | Tuner (DE3) | 28 mU mL$^{-1}$ |
| 18 | pET30a+ | ArcticExpress (DE3) | 21 mU mL$^{-1}$ |

*Note: The activities are mentioned per mL of lysate. 1 U will transform 1 µmol of substrate in 1 hour at 30° C. and pH 7.2

EXAMPLE 20

Isolation of Rebaudioside X

The amount of the product mixture of Example 14 was not large enough to separate via preparative HPLC methods. Accordingly, analytical HPLC with a series of injections was used to separate the components of the mixture. Separation was conducted according to the method described above in Example 14 to provide two fractions corresponding to the two main peaks in the HPLC trace of FIG. 5: Fraction A (retention time 24.165 minutes) and Fraction B (retention time 31.325 minutes).

The retention time of Fraction A was consistent with reb D, indicating unreacted starting material from the biotransformation reaction.

Figure 6:
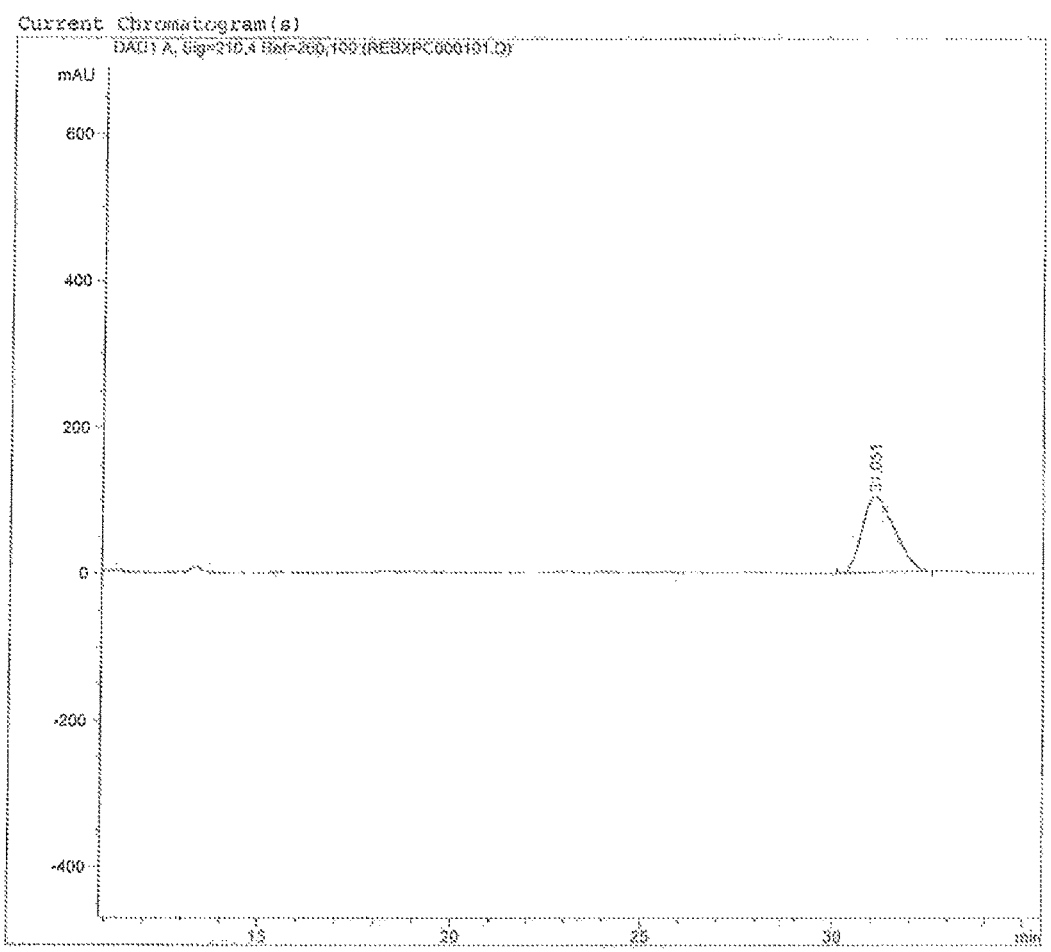
FIG. 6. shows the HPLC chromatogram of purified reb X produced by biocatalysis from reb D.
Figure 7:
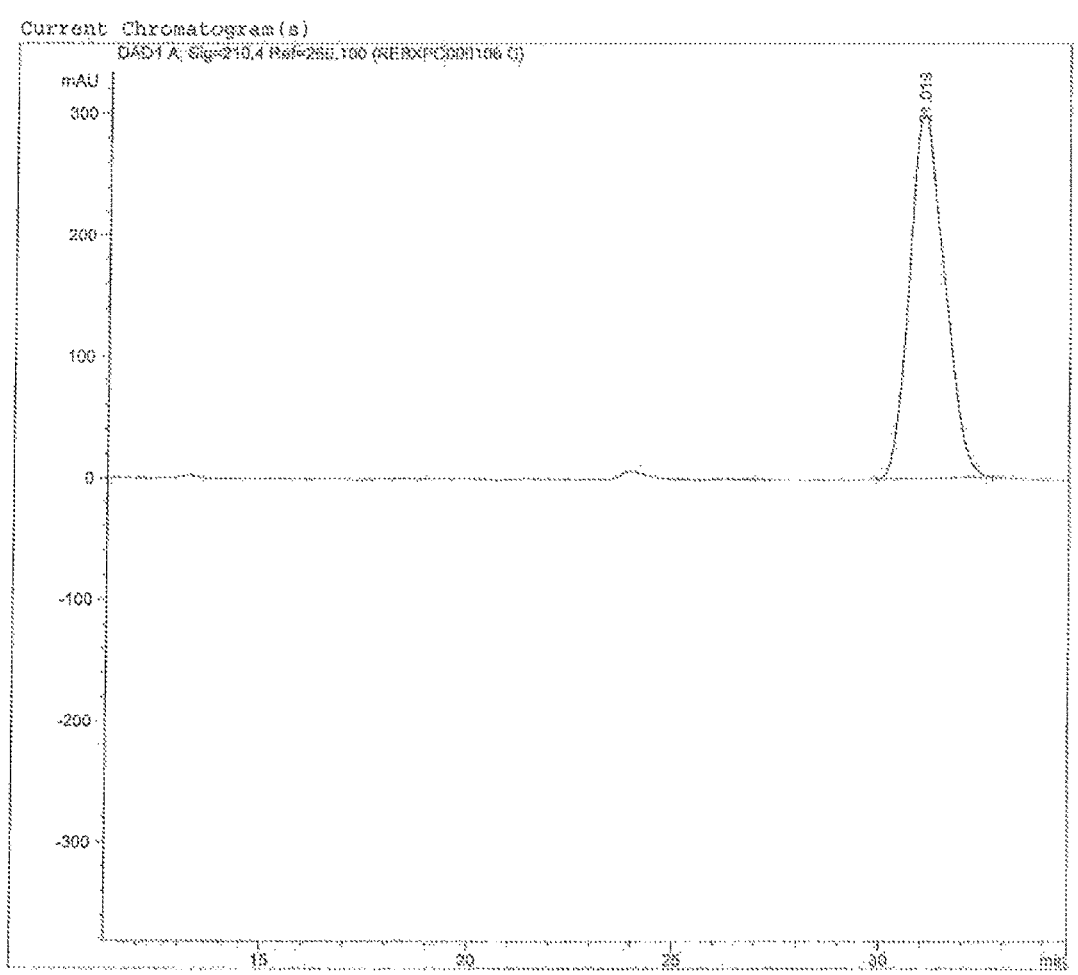
FIG. 7 shows the HPLC chromatogram of a reb X standard.
Figure 8:
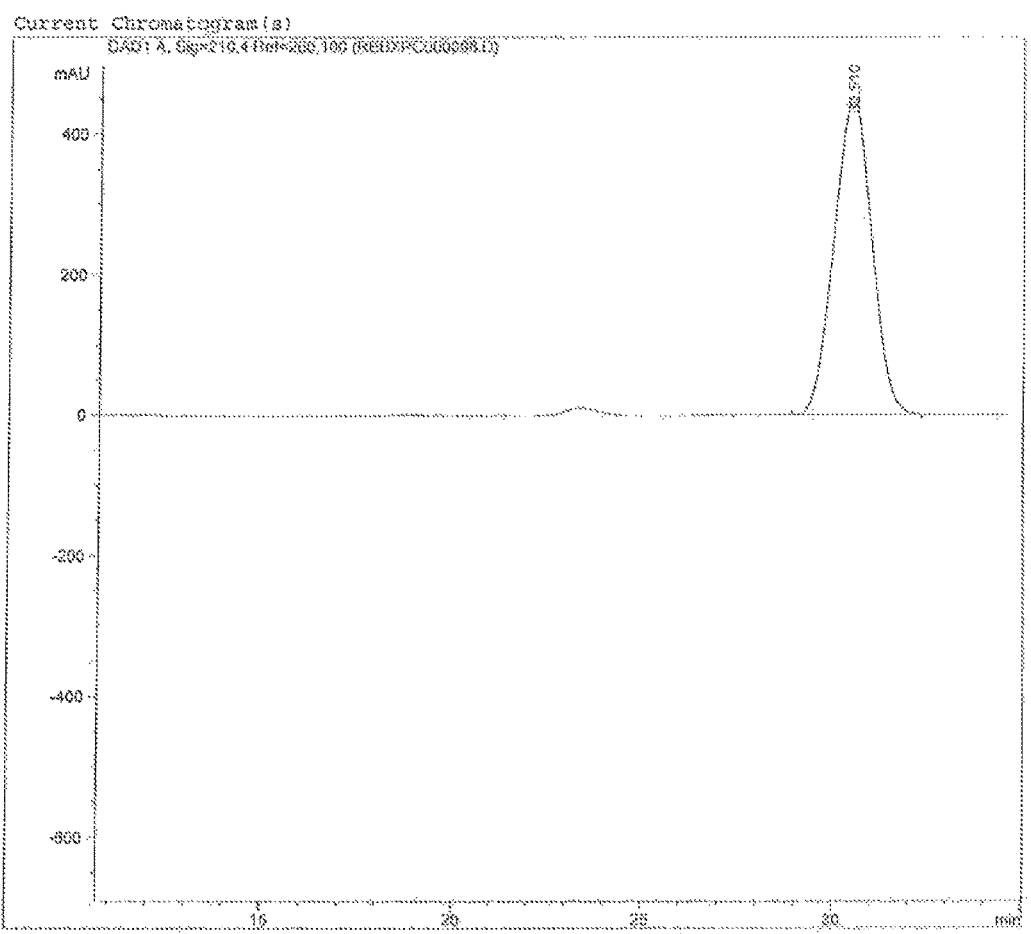
FIG. 8 shows the HPLC chromatogram of co-injection of a reb X standard and reb X purified from biotransformation from reb D.

The retention time of purified Fraction B (FIG. 6) was consistent with reb X, indicating successful biotransformation from reb D. The identity of the material collected in Fraction B as reb X was confirmed by co-injection of purified Fraction B with a reb X standard (available from Pure Circle, HPLC trace of reb X standard shown in FIG. 7). Both Fraction B and the reb X standard were found to elute at the same retention time (FIG. 8), indicating Fraction B was reb X.

The identity of Fraction B as reb X was also separately confirmed by NMR and HRMS. For sampling, Fraction B was concentrated under rotovapor, freeze dried and dried for 40 h at 40° C.

Figure 9:
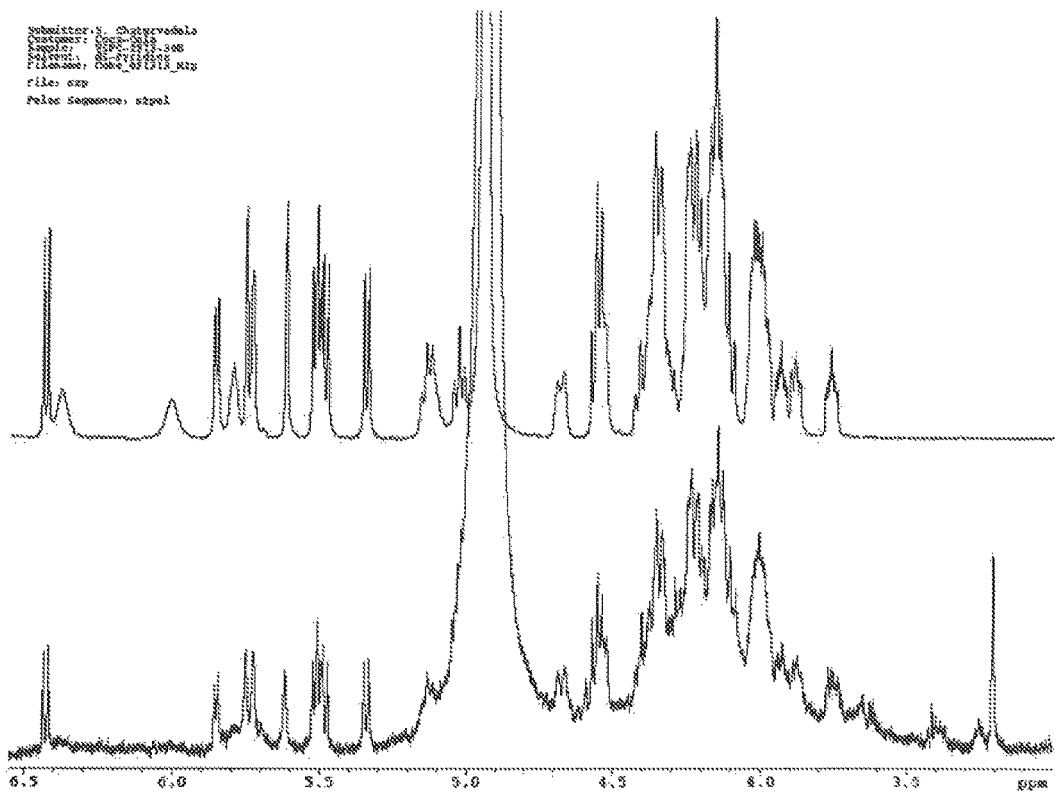
FIG. 9 shows an overlay of the $^1$H NMR spectra of a reb X standard and reb X purified following biosynthesis from reb D.

The NMR sample was dissolved in deuterated pyridine ($C_5D_5N$) and spectra were acquired on a Varian Unity Plus 600 MHz instrument using standard pulse sequences. The NMR spectra of Fraction B was compared to the NMR spectra of reb X. An overlay of the two spectra (FIG. 9) showed consistency of peaks of Fraction B with reb X. A table of the NMR assignments for reb X is shown below:

$^1H$ and $^{13}C$ NMR spectral data for Rebaudioside X in $C_5D_5N^{a-c}$.

| Position | $^{13}C$ NMR | $^1H$ NMR |
|---|---|---|
| 1 | 40.3 | 0.75 t (13.2) |
|  |  | 1.76 m |
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |

| $^1$H and $^{13}$C NMR spectral data for Rebaudioside X in $C_5D_5N^{a-c}$. | | |
|---|---|---|
| Position | $^{13}$C NMR | $^1$H NMR |
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1" | 96.2 | 5.46 d (7.1) |
| 2" | 81.4 | 4.13 m |
| 3" | 87.9 | 4.98 t (8.5) |
| 4" | 70.4 | 4.07 t (9.6) |
| 5" | 77.7 | 3.94 m |
| 6" | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

$^a$assignments made on the basis of COSY, HMQC and HMBC correlations;
$^b$Chemical shift values are in δ (ppm);
$^c$Coupling constants are in Hz.

Figure 10:
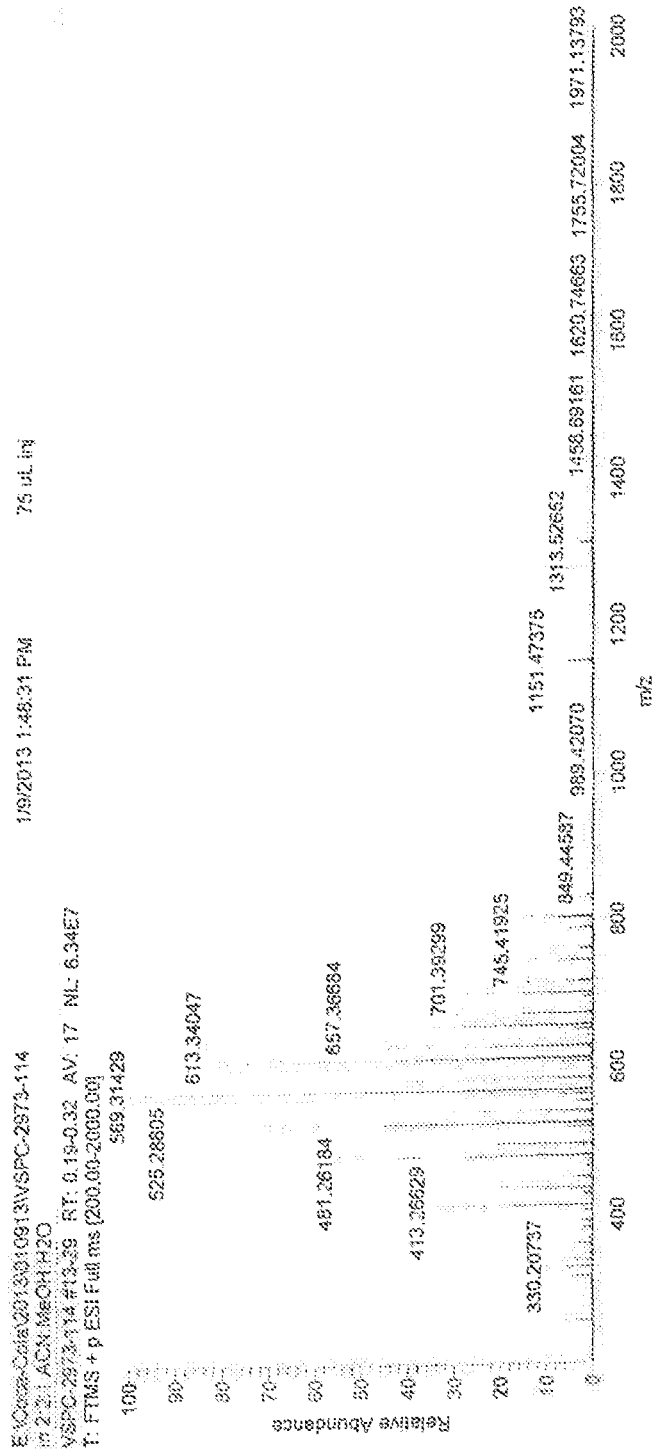
FIG. 10 shows the HRMS spectrum of reb X purified following biocatalytic production from reb D.
Figure 11:
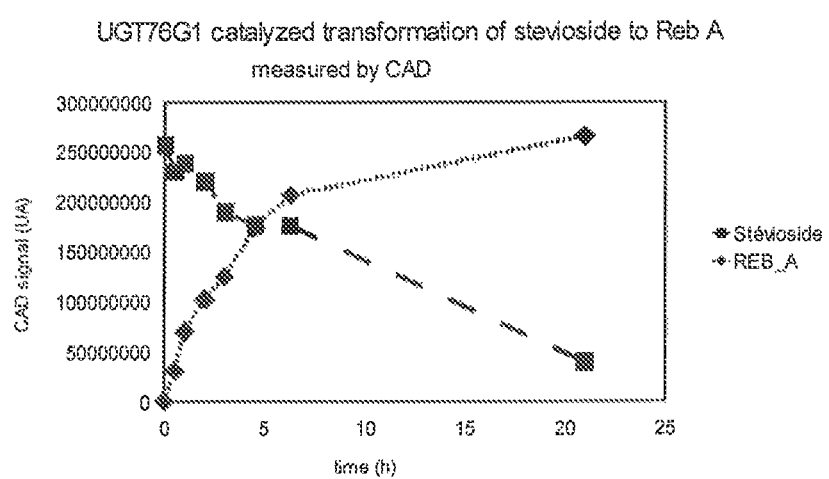
FIG. 11 is a graph showing UGT76G1 catalyzed transformation of stevioside to Reb A measured by CAD.
Figure 12:
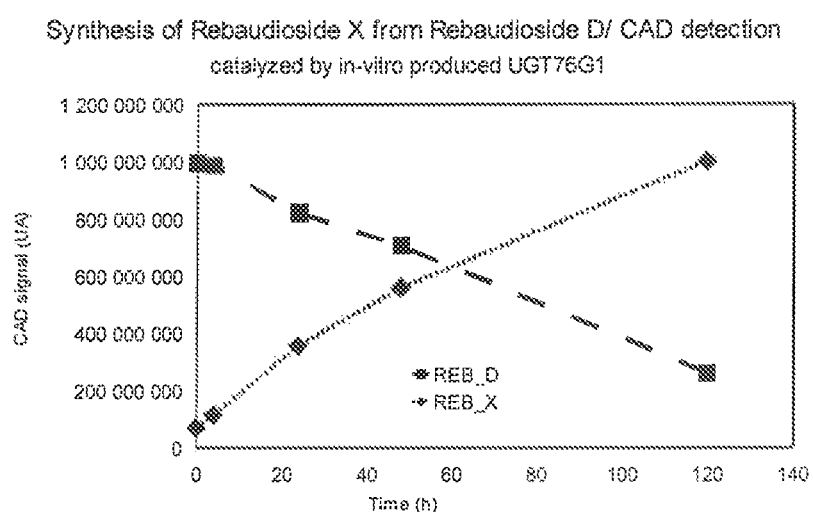
FIG. 12 is a graph showing the synthesis of Rebaudioside X from Rebaudioside D catalyzed by in-vitro produced UGT76G1 using CAD detection.

HRMS (FIG. 10) was generated with a Waters Premier Quadropole Time-of-Flight (Q-TOF) mass spectrometer equipped with an electrospray ionization source operated in the positive-ion mode. The sample was dissolved in methanol and eluted in 2:2:1 methanol:acetonitrile:water and introduced via infusion using the onboard syringe pump. The presence of reb X was confirmed by a [M+Na]$^+$ adduct at m/z 1313.5265, which corresponds to a molecular formula of $C_{56}H_{90}O_{33}$:

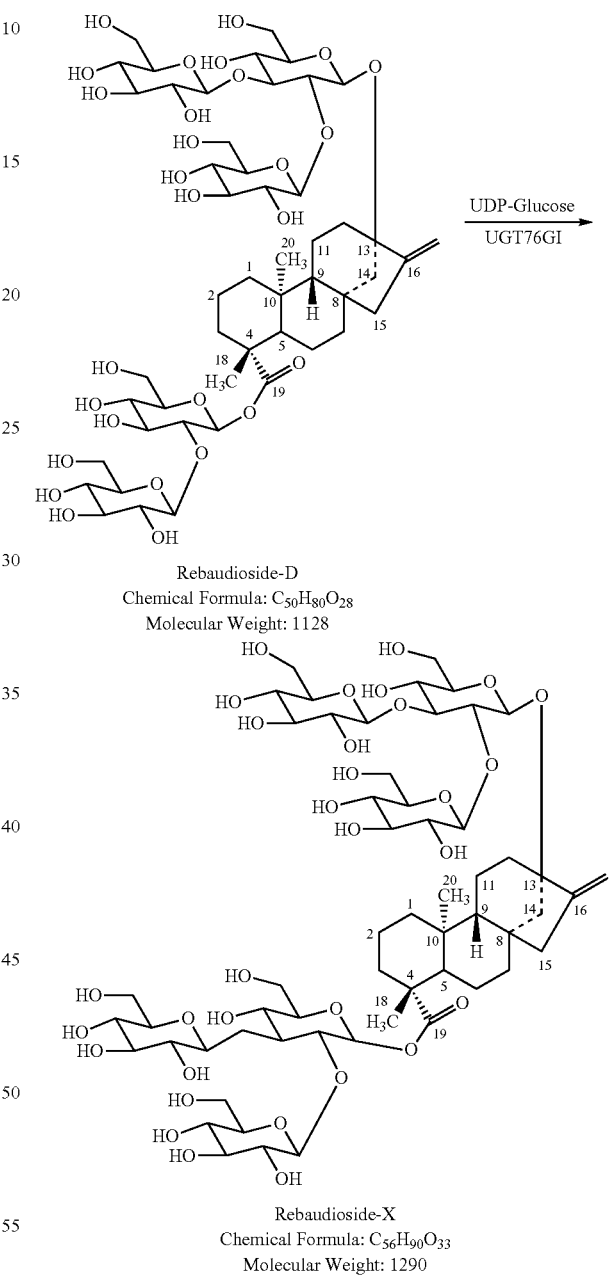

Rebaudioside-D
Chemical Formula: $C_{50}H_{80}O_{28}$
Molecular Weight: 1128

Rebaudioside-X
Chemical Formula: $C_{56}H_{90}O_{33}$
Molecular Weight: 1290

We claim:

1. A method for adding at least one glucose unit to a steviol glycoside substrate to provide a target steviol glycoside, comprising contacting the steviol glycoside substrate with a recombinant biocatalyst protein enzyme comprising UDP-glucosyltransferase, wherein the target steviol glycoside is Rebaudioside X.

2. The method of claim 1, wherein the steviol glycoside substrate is selected from the group consisting of steviolmonoside, steviolbioside, nibusoside, rebaudioside E, rebaudioside Ci, rebaudioside 1, stevioside, rebaudioside A, rebaudioside D, synthetic steviol glycosides and combinations thereof.

3. The method of claim 1, further comprising the step of purifying the Rebaudioside X to a purity of greater than about 80% by weight.

4. The method or claim 1, further comprising the step of purifying, the Rebaudioside X to a purity of greater than about 90% by weight.

5. The method of claim 1, further comprising the step of purifying the Rebaudioside X to a purity of greater than about 95% by weight.

6. The method of claim 1, wherein the UDP-glucosyltransferase is expressed in a host microorganism.

7. The method of claim 6, wherein the host microorganism is selected from the group consisting of: *Escherichia coli, Saccharomyces species, Aspergillus* species, and *Pisehia* species.

* * * * *

UNITED STATES PATENT AND TRADEMARK OFFICE
CERTIFICATE OF CORRECTION

PATENT NO. : 10,485,257 B2
APPLICATION NO. : 15/400325
DATED : November 26, 2019
INVENTOR(S) : Markosyan et al.

Page 1 of 1

It is certified that error appears in the above-identified patent and that said Letters Patent is hereby corrected as shown below:

In the Claims

In Claim 2, Line 3, please delete "nibusoside" and insert --rubusoside-- therefor.

In Claim 2, Line 4, please delete "Ci" and insert --G-- therefor.

In Claim 2, Line 4, please delete "1" and insert --I-- therefor.

In Claim 7, Lines 3 and 4, please delete "Pise-hia" and insert --Pischia-- therefor.

Signed and Sealed this
Twenty-fourth Day of November, 2020

Andrei Iancu
*Director of the United States Patent and Trademark Office*